(12) United States Patent
Sowemimo-Coker et al.

(10) Patent No.: US 7,291,450 B2
(45) Date of Patent: Nov. 6, 2007

(54) PREPARATION OF A CELL CONCENTRATE FROM A PHYSIOLOGICAL SOLUTION

(75) Inventors: Samuel O. Sowemimo-Coker, Dix Hills, NY (US); Marcus Lee Scott, Memphis, TN (US); Marc Long, Memphis, TN (US); Ed Margerrison, Germantown, TN (US); Michael B. Cooper, Memphis, TN (US)

(73) Assignees: Smith & Nephew, Inc., Memphis, TN (US); Pall Corporation, East Hills, NY (US)

( * ) Notice: Subject to any disclaimer, the term of this patent is extended or adjusted under 35 U.S.C. 154(b) by 23 days.

(21) Appl. No.: 10/811,549

(22) Filed: Mar. 29, 2004

(65) Prior Publication Data

US 2005/0205498 A1    Sep. 22, 2005

Related U.S. Application Data

(60) Provisional application No. 60/528,583, filed on Dec. 10, 2003, provisional application No. 60/458,354, filed on Mar. 28, 2003.

(51) Int. Cl.
*A01N 1/02* (2006.01)
*A01N 63/00* (2006.01)

(52) U.S. Cl. ............... 435/2; 424/93.7; 424/93.71; 424/93.72

(58) Field of Classification Search ............... None
See application file for complete search history.

(56) References Cited

U.S. PATENT DOCUMENTS

| | | | |
|---|---|---|---|
| 5,824,084 A | | 10/1998 | Muschler |
| 6,010,627 A | | 1/2000 | Hood, III et al. |
| 6,049,026 A | | 4/2000 | Muschler |
| 6,153,104 A | * | 11/2000 | Robertson ............ 210/650 |
| 6,342,157 B1 | | 1/2002 | Hood, III et al. |
| 6,398,972 B1 | | 6/2002 | Blasetti |
| 6,544,751 B1 | | 4/2003 | Brandwein et al. |
| 7,056,738 B2 | * | 6/2006 | Prockop et al. ............ 435/372 |
| 2002/0179537 A1 | | 12/2002 | Sukavaneshvar et al. |
| 2004/0071668 A1 | * | 4/2004 | Bays et al. ............ 424/93.7 |

FOREIGN PATENT DOCUMENTS

| | | |
|---|---|---|
| EP | 0928617 | 7/1999 |
| WO | WO 96/27397 | 9/1996 |
| WO | WO 00/61256 | 10/2000 |
| WO | WO-00/62840 | 10/2000 |
| WO | 01/72369 | * 10/2001 |
| WO | WO-02/067867 | 9/2002 |
| WO | WO 02/089737 | 11/2002 |

OTHER PUBLICATIONS

Blazsek et al., "Large scale recovery and characterization of stromal cell-associated primitive haemopoietic progenito cells from filter-retained human bone marrow", Bone Marrow Transplantation 23 : 647-657 (1999).*
Merriam-Webster Medical Dictionary online, "solution", accessed Sep. 19, 2006.*
Connolly, John, et al.; Development of an Osteogenic Bone-Marrow Preparation, Journal of Bone and Joint Surgery (Jun. 5, 1989), vol. 71-A, pp. 684-691.
Surgical Autologous Growth Factor Extracts; Nov. 28, 2000.
"The ABC's of Filtration and Bioprocessing for the Third Millennium"; book; Pall Corporation; 2002; Northern Boulevard, East Hills, NY 11548.
Eichler et al., "Engraftment Capacity of Umbilical Cord Blood Cells Processed by Either Whole Blood Preparation or Filtration"; Stem Cells; 2003; pp. 208-216; vol. 21.
Lee at al., "*Wintrobe's* Clinical Hematology"; book; 10th edition; Jan. 15, 1999; pp. 1124-1126 and p. 2741 ; Lippincott Williams & Wilkins; vol. 2; Philadelphia; Baltimore; New York; London; Buenos Aires; Hong Kong; Sydney; Tokyo.
Lucarelli et al., "Platelet-derived growth factors enhance proliferation of human stromal stem cells"; Biomaterials; Aug. 2003; 3095-100; vol. 24(18).
Niyibizi et al., "Novel approaches to fracture healing"; Expert Opinion on Investigational Drugs; Jul. 2000; pp. 1573-1580; vol. 9 (7).
Takigami, et al.; "Spine Fusion Using Allograft Bone Matrix Enriched in Bone Marrow Cells and Connective Tissue Progenitors"; 48th Annual Meeting of the Orthopedic Research Society; The Spine Journal; Sep. 2002; pp. 100; vol. 2(5).
"Filtration and Bioprocessing Products for the Third Millennium", book; Pall Corporation; date accessed 2000, Northern Boulevard, East Hills, NY 11548.

* cited by examiner

*Primary Examiner*—Sandra E. Saucier
(74) *Attorney, Agent, or Firm*—Fulbright & Jaworski, LLP

(57) ABSTRACT

The present invention is directed to methods and compositions regarding the preparation of an cell concentrate, such as, for example, an osteogenic cell concentrate, from a physiological solution, such as bone marrow aspirate, blood, or a mixture thereof. In specific embodiments, the invention provides methods and compositions utilizing two physiological solution-processing techniques, particularly in a point of care environment, wherein centrifugation is not employed.

19 Claims, 27 Drawing Sheets

Back-flush
C  Close valves to collection and drain bags. Open valves to syringes.

D Recover
Backflush osteogenic cells from filter.

A

Attach
Attach syringe filled with physiological solution to a fat reduction filter.

Fill
B  Inject physiological solution through fat reduction filter into collection bag.

D Back-flush
Close valves to collection and drain bag. Open valves to syringes.

E Recover
Backflush osteogenic cells from leukoreduction filter.

B Fill
Inject marrow aspirate through aggregate filter into collection bag.

D Back-flush
Close valves to collection and drain bag. Open valves to syringes.

Recovery Solution

E     Recover
Backflush osteogenic cells from leukoreduction filter.

Blood

Pre-Processed BMA

Post-Processed BMA

PREPARATION OF A CELL CONCENTRATE FROM A PHYSIOLOGICAL SOLUTION

The present application claims priority to U.S. Provisional Patent Application Ser. No. 60/458,354 and to U.S. Provisional Patent Application Ser. No. 60/528,583, filed Dec. 10, 2003, both of which are incorporated by reference herein in their entirety.

FIELD OF THE INVENTION

The present invention generally regards the fields of bone therapy, bone marrow processing, and medicine, such as orthopedic medicine. In a specific embodiment, the present invention is directed to the processing of physiological product, such as bone marrow aspirate, through a dual-step filter system either step of which lacks centrifugation.

BACKGROUND OF THE INVENTION

Bone graft substitutes (BGS) are commonly used as a less-invasive alternative to autograft for the repair of osseous defects. Autograft, however, remains the gold standard in grafting applications due to its supply of a structural scaffold, osteoinductive growth factors, and osteogenic cells. A promising surgical option to autograft is the use of a composite graft consisting of a BGS combined with bioactive (i.e, osteoinductive and osteogenic) elements. Examples of bioactive elements include platelets (which secrete osteoinductive growth factors) and stem cells (which differentiate into osteogenic bone-forming cells). Sources of these bioactive elements include bone marrow aspirate and blood, which are less invasive to procure from a patient than autograft. With this in mind, techniques have been developed to procure and concentrate bioactive elements from bone marrow aspirate and blood for use in tissue healing applications. Centrifugation is typically used to separate osteogenic/osteoinductive cells from other blood constituents based on differences in density. However, preparation of cell-rich suspensions can be arduous in addition to requiring the purchase and maintenance of a centrifuge in the operating room. Accordingly, a point-of-care surgical technique that could concentrate stem cells and platelets from blood or bone marrow aspirate without the need for centrifugation is desirable. This would give a surgeon a convenient method to rapidly prepare a bioactive BGS that would be a viable and less invasive alternative to autograft.

In Connolly et al. (1989), marrow extracted from rabbits was concentrated by simple centrifugation, isopyknic centrifugation, and gravity sedimentation, all of which increased the nucleated cell count on average compared to whole marrow. The osteogenic effect of bone marrow was tested in rabbits, using a chamber that had been implanted in a peritoneal cavity (ectopic site) and in a delayed-union model (orthotopic site). Osteogenesis was accelerated in both sites after concentration of marrow elements after centrifugation, but not after gravity sedimentation. Although a method to increase the nucleated cell density within bone marrow aspirate was described, centrifugation was utilized to concentrate stem cells in marrow. Furthermore, the concentrate was not used in conjunction with an osteoconductive scaffold material.

PCT Patent Application WO 96/27397 provides a plasma-buffy coat concentrate that comprises plasma, platelets, and fibrinogen. When the concentrate is combined with a fibrinogen activator in sufficient concentration to initiate clot formation, a wound sealant is formed. Also provided is a method for processing blood to produce the plasma-buffy coat concentrate. The method comprises centrifuging anticoagulated blood to remove red blood cells and to produce a plasma-buffy coat mixture. Water is removed from the mixture by hemofiltration to produce the plasma-buffy coat concentrate. A fibrinogen activator is mixed with the plasma-buffy coat concentrate to produce a wound sealant that can be used for multiple clinical indications, including bone-grafting applications.

U.S. Pat. Nos. 6,010,627 and 6,342,157 provide a device and a method for concentrating a blood fraction, typically plasma, to provide a concentration of blood procoagulant proteins, such as fibrinogen, and cellular components, such as platelets, white blood cells, or buffy coat cells. Water is removed from plasma by hemofiltration to produce a plasma-buffy coat concentrate. The resultant concentrate is suitable for use in the preparation of coagulum-based wound sealants. The method utilizes a hemofilter, which is a type of hollow fiber filter used for blood processing, in order to concentrate cells and proteins within a blood fraction. The prior art defines an ultrafiltration unit having a semi-permeable membrane with a molecular weight cut-off of about 30,000 daltons, which allows for the concentration of fibrinogen protein, useful for coagulation upon addition of a fibrinogen activator to the cell/protein concentrate. However, U.S. Pat. Nos. 6,010,627 and 6,342,157 do not describe the fiber filter for the concentration of mesenchymal stem cells and platelets from either whole blood or bone marrow aspirate. Accordingly, a larger cut-off filter (i.e., exceeding 30,000 daltons) may be used in the present invention to concentrate cells since the recovery of proteins is not critical. Because larger cut-off filters have higher flow rates and require lower operating pressure than smaller cut-off filters, the filters in the present invention will require less time and force to operate compared to the filters disclosed therein.

Muschler et al. (2002; U.S. Pat. Nos. 5,824,084 and 6,049,026) provide a method for preparing a composite BGS in which bone marrow aspirate is passed through a porous substrate. The osteoprogenitor cells are selectively retained in the substrate, resulting in a composite graft that contains an enriched (i.e., greater) number of progenitor cells compared to an equivalent volume of bone marrow aspirate. A method is provided for passing marrow through an implantable porous scaffold that acts as an affinity column for mesenchymal stem cells. The stem cells are selectively retained in the substrate, resulting in a composite graft that contains an enriched (i.e., greater) number of stem cells compared to an equivalent volume of bone marrow aspirate. However, the disclosure of Muschler does not describe methods and compositions for the enrichment of platelets.

PCT Patent Application WO 00/61256 and U.S. Pat. No. 6,398,972 describe an automated method and apparatus for producing platelet-rich plasma or a platelet concentrate from a physiological solution, preferably blood. Processing is carried out by a centrifuge that receives a disposable container having two chambers. Whole blood is placed into one of the two chambers, and the centrifuge is then operated to cause the red blood cells to sediment to the bottom of one chamber, resulting in a supernatant of platelet-rich plasma. The centrifugation is stopped, which causes the platelet-rich plasma to drain to the second chamber. The platelet-rich plasma in the second chamber is then centrifuged a second time by restarting the centrifuge. The centrifuge is stopped, resulting in: (1) red blood cells in one chamber; (2) platelet concentrate at the bottom of the second chamber; and (3) platelet poor plasma as the supernatant in the second chamber. A portion of the platelet poor plasma is removed from the second chamber, leaving a remaining portion of the platelet poor plasma and platelet concentrate in the second chamber. The remaining platelet concentrate is suspended in the platelet-poor plasma remaining in the second chamber to obtain platelet rich plasma.

Thus, the present invention as described herein provides a need in the art of clinical therapy, particularly bone therapy, lacking in the present methods.

BRIEF SUMMARY OF THE INVENTION

The present invention is directed to a system, method, and compositions that are beneficial for use in the repair of, for example, osseous defects. More particularly, the present invention provides a method to prepare a cell concentrate from a physiological solution (preferably bone marrow aspirate, blood, or a mixture thereof) at the point of care and, optionally, without the need for centrifugation. Although the cell concetrate is preferably utilized for osteogenic treatments, in alternative embodiments the cell concentrate is analyzed, such as for diagnosis, drug testing, or prognosis purposes, for example.

In a particular embodiment of the invention, there is a method of preparing a cell concentrate, comprising the steps of providing a physiological solution not previously subjected to centrifugation; subjecting said physiological solution to a filter to produce a filter retentate and a permeate solution, wherein said filter retentate comprises platelets, nucleated cells, or both per unit volume greater than in the physiological solution and wherein said permeate solution comprises plasma and red blood cells; and removing the filter retentate from the filter. In a specific aspect, the filter is a leukocyte reduction filter.

In specific embodiments, the providing step may be further defined as combining an additional solution with the physiological solution, wherein the additional solution comprises water or a hypotonic solution, such as sodium chloride.

In another embodiment of the present invention, there is a method of preparing a cell concentrate, comprising the steps of providing a physiological solution; subjecting the physiological solution to a first filtration device to isolate nucleated cells, platelets, or both from the physiological solution, the isolating step producing a first product; and subjecting said first product to a second filtration device to produce a second product, the second product comprising a number of nucleated cells, platelets, or both per unit volume greater than in the physiological solution. In a specific embodiment, the first filtration device is a nucleated cell filtration device, which may be further defined as a leukocyte reduction filtration device, and in another specific embodiment, the second filtration device is further defined as a hollow fiber filtration device.

A filtration device, such as, for example, the second filtration device, may comprise a pore size between about 0.05 µm and about 5 µm or, more preferably between about 0.2 µm and about 0.5 µm.

Methods of the invention lack a centrifugation step, in preferred embodiments.

The physiological solution comprises bone marrow aspirate, blood, or a mixture thereof, in specific embodiments, and in some embodiments the nucleated cells comprise stem cells, connective tissue progenitor cells, osteoprogenitor cells, chondroprogenitor cells, or a mixture thereof. The stem cells are mesenchymal stem cells, hematopoietic stem cells, or both, in some embodiments. In other embodiments the method further comprises the step of delivering the second product to a bone defect in an individual and/or comprises the step of admixing a scaffold material to said second product to produce a scaffold material/second product mixture. In some embodiments, the method may also comprise the step of delivering the scaffold material/second product mixture to a bone defect in an individual.

The scaffold material may be comprised of a block, paste, dust, cement, powder, granule, putty, liquid, gel, solid, or a mixture thereof and/or it may be comprised of a ceramic, a polymer, a metal, allograft bone, autograft bone, demineralized bone matrix, or a mixture thereof. The scaffold material may be biodegradable and is preferably osteoconductive, osteoinductive, or osteogenic. In a specific embodiment, the scaffold material is comprised of synthetic material, natural material, or a combination thereof.

In a specific embodiment, the method further comprises the step of admixing a biological agent with the second product, the scaffold material, or a combination thereof, and the biological agent admixed with the scaffold material may be further defined as the biological agent being comprised on the scaffold material, in the scaffold material, or both. In particular embodiments, the scaffold material itself is the biological agent.

In another embodiment of the present invention, there is a cell concentrate generated by methods described herein.

In an additional embodiment of the present invention, there is a method of increasing nucleated cell concentration and/or platelet concentration from a physiological solution, comprising the steps of providing a physiological solution; subjecting the physiological solution to a nucleated cell filtration device to isolate nucleated cells, platelets, or both from the physiological solution, the isolating step producing a first product; and subjecting the first product to a fibrous filtration device to produce a second product, the second product comprising a number of nucleated cells, platelets, or both per unit volume greater than in the physiological solution.

The providing the bone marrow aspirate step may be further defined as aspirating the bone marrow from an individual into a first syringe to produce a bone marrow aspirate. Preferably, the first syringe comprises an anti-coagulant, an isotonic solution, or both.

In a further specific embodiment, the subjecting the bone marrow aspirate to a nucleated cell filtration device is further defined as introducing the bone marrow aspirate to a first housing device, said first housing device connected in-line to a leukocyte reduction filter and said leukocyte reduction filter connected in-line to a second housing device, wherein the leukocyte filter permits passage of plasma and red blood cells through said filter but inhibits passage of nucleated cells, platelets, or both; introducing a purge solution to the filter to produce a purge solution/nucleated cell/platelet mixture; and retrieving the purge solution/nucleated cell/platelet mixture from said filter.

The subjecting the first product to a filtration device may comprise subjecting the first product to a hollow fiber filtration device and/or the subjecting the first product to a filtration device may comprise subjecting the first product to the filtration device, the device comprising a filter, wherein the feed direction of the first product through the filtration device is nonparallel to the flow of the first product across the membrane.

In a specific embodiment, the providing the blood step may be further defined as aspirating the blood from an individual into a first syringe to produce a blood aspirate, for example. The first syringe may comprise an anti-coagulant, an isotonic solution, or both. In a specific embodiment, the subjecting the blood aspirate to a nucleated cell filtration device is further defined as introducing the blood aspirate to a first housing device, said first housing device connected in-line to a leukocyte reduction filter and said leukocyte reduction filter connected in-line to a second housing device, wherein the leukocyte filter permits passage of plasma and red blood cells through said filter but inhibits passage of nucleated cells, platelets, or both; introducing a purge solution to the filter to produce a purge solution/nucleated cell/platelet mixture; and retrieving the purge solution/nucleated cell/platelet mixture from said filter.

The providing the bone marrow aspirate/blood mixture step may be further defined as aspirating the bone marrow and blood from an individual into a first syringe to produce a bone marrow aspirate/blood aspirate. The first syringe may comprise an anti-coagulant, an isotonic solution, or both. The subjecting the bone marrow aspirate/blood aspirate to a nucleated cell filtration device may be further defined as introducing the bone marrow aspirate/blood aspirate to a first housing device, said first housing device connected in-line to a leukocyte reduction filter and said leukocyte reduction filter connected in-line to a second housing device, wherein the leukocyte filter permits passage of plasma and red blood cells through said filter but inhibits passage of nucleated cells, platelets, or both; introducing a purge solution to the filter to produce a purge solution/nucleated cell/platelet mixture; and retrieving the purge solution/nucleated cell/platelet mixture from said filter.

In an additional embodiment of the present invention, there is a method of treating a bone defect in an individual, comprising the steps of obtaining a physiological solution comprising nucleated cells, platelets, or both; subjecting the physiological solution to a nucleated cell-filtration device to isolate nucleated cells, platelets, or both, said isolating step producing a first product; subjecting the first product to a hollow fiber filtration device to produce a second product, the second product comprising a number of nucleated cells, platelets, or both per unit volume greater than in the physiological solution; and delivering the second product to the bone defect in the individual. The method lacks a centrifugation step, in specific embodiments, although in alternative embodiments a centrifugation step is utilized, such as, for example, to remove adipocytes and non-cellular fatty matter from the platelets and nucleated cells.

The bone defect may comprise a break, fracture, void, diseased bone, loss of bone, brittle bone, weak bone, bone injury, or bone degeneration. The method may further comprise the step of admixing a scaffold material with the second product. The physiological solution is blood, bone marrow aspirate, or a mixture thereof, in some embodiments.

The physiological solution is preferably obtained from the individual. In a specific embodiment, the method occurs at a point-of-care in a hospital facility or a health care provider facility. In another specific embodiment, the method further comprises administering to the individual an additional bone defect therapy. The additional bone defect therapy comprises fracture repair, surgery, bone excision, implant delivery, external stimulation, or a combination thereof. In specific embodiments, the nucleated cells comprise leukocytes, stem cells, connective tissue progenitor cells, osteoprogenitor cells, chondroprogenitor cells, or a mixture thereof. The stem cells may be mesenchymal stem cells, hematopoietic stem cells, or a mixture thereof. The delivering the second product to the individual may comprise applying the second concentrated product directly to the bone defect. In a specific embodiment, the applying is with a scoop, scoopula, syringe, rod, or spatula.

In another specific embodiment, the method further comprises the step of admixing a biological agent with the second product, the scaffold material, or a combination thereof. The biological agent admixed with the scaffold material may be further defined as the biological agent being comprised on the scaffold material, in the scaffold material, or both.

In an additional embodiment of the present invention, there is a method of preparing an osteogenic cell concentrate from a physiological solution comprising subjecting the physiological solution to at least one filtration step, wherein the method preferably lacks centrifugation.

In another embodiment, there is a kit for preparing a cell concentrate, comprising a first filtration device and a second filtration device, both of which are housed in a suitable container. In a specific embodiment, the first filtration device and second filtration device are housed in a suitable container. In another specific embodiment, the first filtration device is a nucleated cell filtration device and/or the second filtration device is a microfiltration device. The microfiltration device may be further defined as a hollow fiber filtration device.

The kit may further comprise a scaffold material housed in a suitable container and/or the kit may further comprise a biological agent housed in a suitable container.

In another embodiment of the present invention, there is a kit for treating a bone defect, comprising a plurality of cells housed in a suitable container, wherein said cells are nucleated cells, platelets, or both. The kit further comprises a scaffold material housed in a suitable container, in specific embodiments. The kit may further comprise a biological agent housed in a suitable container.

In another embodiment of the present invention, there is a kit comprising an apparatus for the preparation of a cell concentrate obtained by a method described herein.

In a particular embodiment, there is a method of preparing a cell concentrate, comprising the steps of providing a physiological solution not previously subjected to centrifugation; subjecting the physiological solution to a leukocyte reduction filter to produce a filter retentate and a permeate solution, wherein the filter retentate comprises platelets, nucleated cells, or both per unit volume greater than in the physiological solution and wherein the permeate solution comprises plasma and red blood cells; and removing the filter retentate from the filter.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings, in which.

DETAILED DESCRIPTION OF THE INVENTION

I. Definitions

Figure 1:
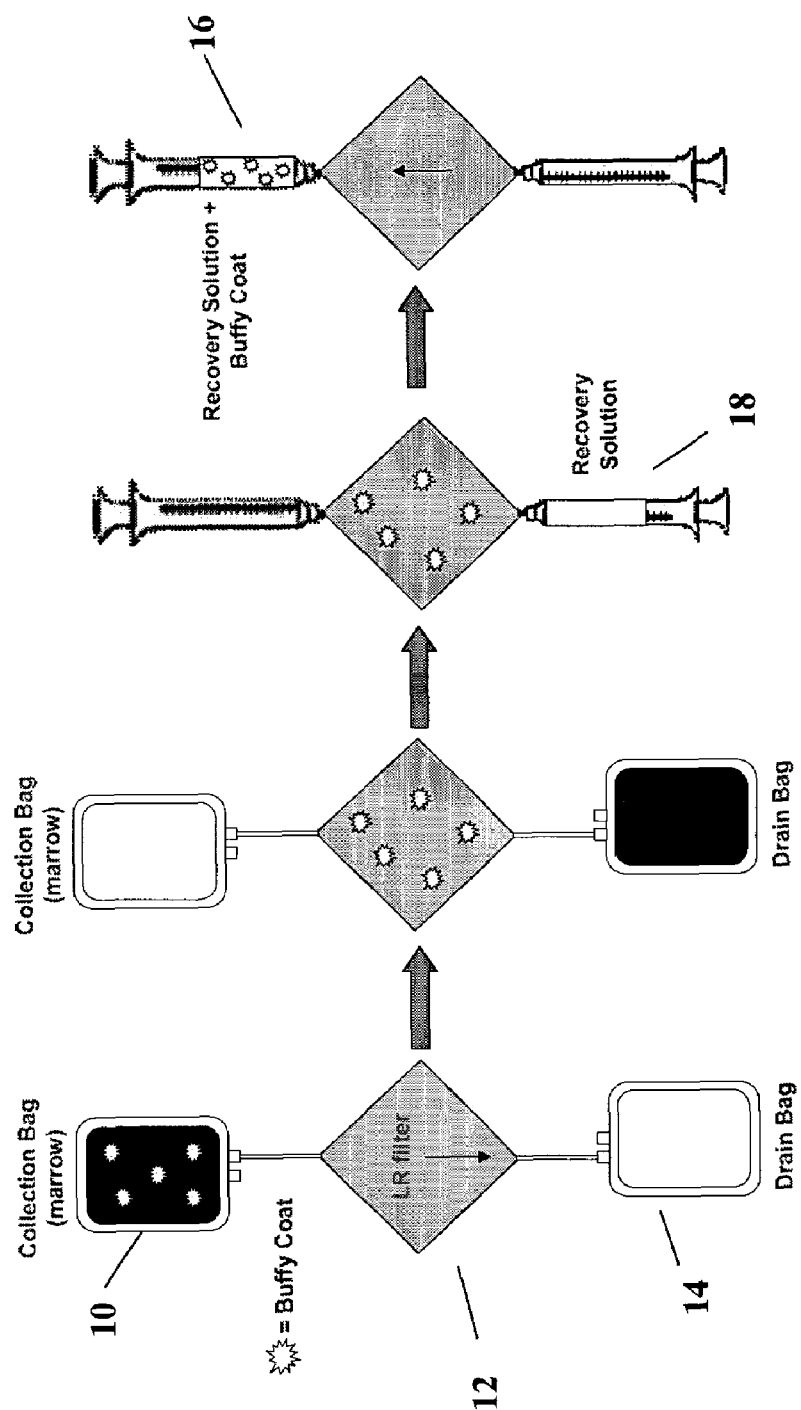
FIG. 1 provides an exemplary schematic showing the filtration of marrrow aspirate through a leukocyte reduction filter to selectively isolate nucleated cells (including mesenchymal stem cells) and/or platelets from a physiological solution.

As used herein the specification, "a" or "an" may mean one or more. As used herein in the claim(s), when used in conjunction with the word "comprising", the words "a" or "an" may mean one or more than one. As used herein "another" may mean at least a second or more. Furthermore, as used herein, the terms "including", "containing", and "having" are open-ended in interpretation and interchangeable with the term "comprising".

The term "allograft bone material" as used herein is defined as bone tissue that is harvested from another individual of the same species. Allograft tissue may be used in its native state or modified to address the needs of a wide variety of orthopaedic procedures. The vast majority of allograft bone tissue is derived from deceased donors. Bone is about 70% mineral by weight. The remaining 30% is collagen and non collagenous proteins (including bone morphogenic proteins, BMPs). Allograft bone that has been cleaned and prepared for grafting provides a support matrix to conduct bone growth, but is not able to release factors that induce the patient's biology to form bone cells and create new bone tissue. In a preferred embodiment, the allograft is cleaned, sanitized, and inactivated for viral transmission.

The term "biological agent" as used herein is defined as an entity that is added to the bone graft substitute to effect a therapeutic end, such as facilitation of bone ingrowth, prevention of disease, administration of pain relief chemicals, administration of drugs, and the like. Examples of biological agents include antibiotics, growth factors, fibrin, bone morphogenetic factors, angiogenic factors, bone growth agents, bone proteins, chemotherapeutics, pain killers, bisphosphonates, strontium salt, fluoride salt, magnesium salt, and sodium salt.

The term "blood" as used herein refers to circulating tissue composed of a fluid portion (plasma) with suspended formed elements (red blood cells, white blood cells, platelets). In a specific embodiment of the invention, the physiological solution refers to whole blood, such as, for example, that provided by a donor, obtained from the circulatory system of a patient, or a mixture thereof. The blood may be obtained by any suitable means, such as in the form of a blood aspirate, for example.

The term "bone graft substitute (BGS)" as used herein is defined as an entity for replacing bone tissue and/or filling spaces in a bone tissue. The term "bone defect" as used herein is defined as a bone defect such as a break, fracture, void, diseased bone, loss of bone, brittle bone or weak bone, injury, disease or degeneration. Such a defect may be the result of disease, surgical intervention, deformity or trauma. The degeneration may be as a result of progressive aging. Diseased bone could be the result of bone diseases such as osteoporosis, Paget's disease, fibrous dysplasia, osteodystrophia, periodontal disease, osteopenia, osteopetrosis, primary hyperparathyroidism, hypophosphatasia, fibrous dysplasia, osteogenesis imperfecta, myeloma bone disease and bone malignancy. The bone deficiency may be due to a disease or condition, such as a disease that indirectly adversely affects bone. Furthermore, the bone malignancy being treated may be of a primary bone malignancy or may be metastatic, originating from another tissue or part of the body.

The term "bone marrow" as used herein refers to soft, gelatinous tissue that fills bone cavities. It is comprised of red bone marrow, which comprises stem cells, progenitor cells, precursor cells, and functional blood cells, and yellow bone marrow, which mainly stores fats. Thus, red bone marrow is myeloid tissue that is actually producing blood cells. Red marrow produces red blood cells, white blood cells, and platelets. A skilled artisan is aware that children comprise much red marrow throughout the body, but in adults it is most concentrated in the flat bones, such as the hipbone. Leukocytes (white blood cells) are also produced in bone marrow and, in some embodiments, are involved in immune defenses. In fact, marrow transplants can treat some types of immunodeficiency. Bone marrow is also referred to as medulla ossium. In a specific embodiment, the bone marrow comprises bone marrow aspirate (bone marrow drawn via syringe from an individual's bone), which a skilled artisan recognizes inevitably contains some peripheral blood.

The term "bone marrow aspirate" as used herein refers to the material obtained upon aspirating bone marrow from a bone, such as by needle.

The term "nucleated cell/platelet fraction" as used herein refers to a solution derived from bone marrow, blood, or a mixture thereof that comprises at least nucleated cells and/or platelets. The nucleated cell fraction comprises mesenchymal stem cells, nucleated connective tissue progenitor cells, nucleated hematopoietic cells, or endothelial cells, or a mixture thereof. In a specific embodiment, the fraction comprises leukocytes. In a specific embodiment, the nucleated cell/platelet fraction does not substantially comprise plasma or red blood cells. The final cell concentration in some embodiments will contain by volume less than approximately 30% of the original plasma and RBC volume. The cell fraction (which may contain some plasma and red cells) can be made to coagulate by mixing it with an appropriate clotting initiator, such as following the filtration steps and prior to application to a bone defect. An ionic calcium solution (such as calcium chloride solution) and/or thrombin could initiate clotting to form a coagulum.

The term "centrifugation" as used herein refers to the rotation in a compartment of an apparatus, said compartment spun about an axis for the purpose of separating materials.

The term "concentrate" as used herein refers to a composition that comprises a greater concentration of a specific component, for example, a particulate or particulates, compared to a parent source.

The term "cross-flow filtration" or "cross-flow mode" as used herein refers to tangential flow filtration, which regards the recirculation of a retentate across the surface of the membrane filter. In specific embodiments, it refers to the direction of feed of a product through a device being perpendicular to the direction of flow across the membrane. In some embodiments the term is defined as filtration comprising multiple passes over a membrane.

The term "dead-end filtration" or "dead-end mode" as used herein refers to filtration wherein the direction of feed of the product and the direction of flow across the membrane are parallel. In some embodiments the term is defined as filtration comprising a single pass over a membrane. In other embodiments, dead-end filtration comprises substantially no tangential flow filtration.

The term "filter retentate" as used herein refers to the composition that is retained by a filter upon passage of a physiological solution across the filter. In particular embodiments, it comprises nucleated cells, platelets, or both. In certain embodiments, the filter retentate comprises very minor amounts of plasma and/or red blood cells. In a specific embodiment, the volume of a filter retentate is about 1 mL or greater.

The term "filtration" as used herein refers to the process of passing a liquid comprising particular matter through a porous material for the purpose of separating the liquid from at least some of the particular matter, for separating some particular matter from other particular matter, or both.

The term "hollow fiber filtration device" as used herein is a filtration device comprising a hollow tubular outer covering, wherein inside the hollow tubular outer covering there are individual tubes whose walls are filters; the individual tubes lay in a direction parallel to the length of the tube. In specific embodiments, the direction of feed of a product through a device is perpendicular to the direction of flow across the membrane. In some embodiments it generally comprises tangential flow filtration, which regards the recirculation of a retentate across the surface of the membrane filter. In alternative embodiments, there is no tangential flow filtration.

The term "mesenchymal stem cell" as used herein refers to pluripotent progenitor cells located in bone marrow that can differentiate into a variety of non-hematopoietic tissues including bone, cartilage, tendon, fat, muscle, and early progenitors of neural cells.

The term "microfiltration" as used herein refers to separation of particles from a fluid, wherein at least one microfiltration device comprises at least one filter having a pore size of about 0.05 µm to about 5 µm. In a specific embodiment of the present invention, cells and/or cell fragments are separated from at least some fluid, wherein the microfiltration capabilities of the filter permit passage of the fluid through the pores, thereby retaining the cells and/or cell fragments.

The term "osteoconductive" as used herein refers to the ability of a material, such as a scaffold material, to allow new bone ingrowth.

The term "osteogenic" as used herein refers to a material that stimulates growth of new bone tissue.

The term "osteoinductive" as used herein refers to the ability to form bone in an ectopic (i.e., non-bony) body site.

The term "permeate solution" as used herein refers to the particles and liquid that is smaller than the pore size of a filter and therefore passes through the filter membrane.

The term "plasma" as used herein refers to blood plasma, which is the pale yellow fluid component of whole blood comprising water, proteins, electrolytes, sugars, lipids, metabolic waste products, amino acids, hormones, and/or vitamins.

The term "purge solution" as used herein refers to a solution that facilitates exodus of a bone marrow or blood derived cells from a filter. In specific embodiments, the purge solution is comprised at least in part of an isotonic saline solution or a colloidal solution such as albumin or dextran, or a mixture thereof. A skilled artisan recognizes that the purge solution may be comprised of water, electrolytes, proteins, carbohydrates, and/or gelatin, and so forth.

The term "scaffold material" as used herein refers to a material that facilitates bone growth upon administration to a bone defect with a osteogenic concentrate, such as is derived from a bone marrow. In a specific embodiment, the scaffold material is comprised at least in part of a synthetic material, a natural material, or both. In further specific embodiments, the scaffold material is comprised of biocompatible material that facilitates, permits, or enhances the laying down of new bone matrix, bone growth and/or bone ingrowth. In additional specific embodiments, ceramics, such as calcium sulfate or calcium phosphate, a polymer, a metal, allograft bone, autograft bone, demineralized bone matrix, a mixture thereof, and so forth. In more specific embodiments, the scaffold material may be a block, paste, cement, powder, granule, putty, gel, or so forth. In a specific embodiment, the scaffold material is osteoconductive, osteoinductive, osteogenic, or a combination thereof. In other embodiments, the scaffold material breaks down over time when placed in the body. In additional specific embodiments, the scaffold material is considered a matrix, a carrier, a solution, a solid, a gel, and the like. In specific embodiments, the scaffold matrix comprises a viscous hydrogel, such as, for example, a carboxymethylcellulose-based hydrogel. In a specific embodiment, the scaffold matrix comprises a JAX® Advanced Bone Void Filler, and/or or JAX®-tcp (tri-calcium phosphate). In additional specific embodiments, the scaffold material comprises a plurality of JAX® toy jack shaped bone graft substitutes. The scaffold material may be a dust, powder, granule, chip, putty, tablet, mixture thereof, and so forth.

The term "second filter" as used herein refers to a filter that is subsequent to a first filter in a process comprising concentrating cells. In particular embodiments, at least one additional step may be included between the first and second filters, and in alternative embodiments this at least one additional step may comprise use of a filter. Further steps to concentrate the cells may be utilized following the second filter.

The term "serum" as used herein refers to the aqueous component of an animal fluid remaining after coagulation (that is, remaining after clot formation removes fibrinogen, prothrombin, and other clotting factors from blood plasma).

The term "stem cell" as used herein refers to an unspecialized cell that gives rise to a specific specialized cell.

II. The Present Invention

The present invention provides novel methods and compositions directed to the generation and/or enrichment of a cell concentrate, such as an osteogenic cell concentrate, from a physiological solution, such as bone marrow aspirate, blood, or a mixture thereof. The procedure employs a system wherein the physiological solution is processed through at least one filtration step, and the system preferably lacks centrifugation. However, in alternative embodiments centrifugation may be utilized.

Thus, in some embodiments the methods of the present invention comprise only one filtration step. In other embodiments, the methods of the present invention comprise two or more filtration steps. In one embodiment of the present invention, there is a method of preparing a cell concentrate by providing a physiological solution and subjecting it to a filter to produce a filter retentate and a permeate solution, wherein the filter retentate comprises platelets, nucleated cells, or both per unit volume greater than in the physiological solution and wherein said permeate solution comprises plasma and red blood cells. Following this filtration step, the filter retentate may comprise substantially the majority of platelets and nucleated cells from the original physiological solution, and the permeate solution may comprise substantially the majority of plasma and red blood cells from the original physiological solution. Regarding the filter retentate, there is at least about a four-fold, five-fold, six-fold, seven-fold, or more increase in concentration of platelets and/or nucleated cells over that of the physiological solution from which they are filtered. In other terms, about 60%, 65%, 70%, 75%, 80%, 85%, 90%, 95%, 97%, or 99% of platelets and/or nucleated cells are filtered from the physiological solution using methods of the present invention. Regarding the permeate solution, about 70%, 75%, 80%, 85%, 90%, 95%, 97%, or 99% of plasma and red blood cells are filtered from the physiological solution, which may be defined as thereafter being present in the permeate solution following filtration, using methods of the present invention.

In one embodiment of the present invention, a single filtration step of a physiological solution concentrates nucleated cells, including leukocytes, and platelets while concomitantly removing plasma and red blood cells from the physiological solution. The resultant concentrate from this single step may be applied directly to a bone defect, processed further using a non-filtration step (such as, for example, adding a biological agent), combined with a scaffold material before application to the bone defect, or subjected to at least one more filtration step, such as to further concentrate the cells and/or exchange the solution in which the cells are comprised.

A skilled artisan recognizes based on the disclosure provided herein that a use of the invention is to obtain a concentrated composition of platelets and nucleated cells, including leukocytes, from a physiological solution. This is in contrast to many known processes in the art that remove leukocytes from blood, for example, as being undesired. The filter retentate comprising the leukocytes is the desired composition, as opposed to a composition to be discarded. In other words, the present invention removes leukocytes from a physiological solution such as blood for the purpose of utilizing them, as opposed to being part of a waste product. This relates to a specific embodiment of the invention being providing cells that release growth factors, such as leukocytes and platelets, which upon administration to a bone defect results in cell migration to the wound, cell proliferation, and differentiation into bone cells. The known blood processing methods that discard leukocytes are trying to reduce or inhibit an immunogenic response, given that the ultimate destination for the composition is for systemic administration to an individual, such as one requiring a blood transfusion. In contrast, the present invention relates to local administration to a wound, as opposed to systemic circulation, such as, for example, with autotransfusion of a cell concentrate to a bone defect.

In other embodiments, the invention is unique in that it is the first to combine two existing blood processing techniques (leukocyte reduction filtration and hollow fiber filtration) into one method in order to increase nucleated cell count (which can include mesenchymal stem cells, connective tissue progenitor cells, chondroprogenitor cells, and/or osteoprogenitor cells) and platelet concentration, optionally without the need for centrifugation. Furthermore, when the concentrated physiological solution is combined with a scaffold material, such as an osteoconductive material, the invention results in a composite BGS that enhances the formation of new bone compared to the scaffold or cell concentrate alone. In additional specific embodiments, the cell concentrate is mixed with a compound, such as with a powder or liquid, to form an injectable putty, which may optionally comprise at least one clotting initiator. Examples of clotting initiators are solutions comprising calcium ions (e.g., calcium chloride solution) or thrombin, or both. In further specific embodiments, a biological agent is combined with the cell concentrate, the scaffold material (in the material, on the material, or both), or the mixture thereof prior to or upon administration to the bone defect.

Although there are methods in the art that employ centrifugation to concentrate stem cells for use as an osteogenic bone marrow preparation, the current invention employs filtration to concentrate both nucleated cells (including stem cells) and platelets, resulting in a marrow concentrate. This filtration optionally obviates costs associated with purchasing and maintaining a centrifuge in the surgery room, and it is also a less arduous method for processing marrow than the centrifugation methods used by others. Furthermore, the current invention provides a method for concentrating both osteogenic (mesenchymal stem cells) and osteoinductive (platelets) elements of bone marrow, whereas known methods regard concentration of one or the other, but not both.

In comparison, the present invention disclosed herein uses filters, not implantable scaffolds, to isolate and concentrate both stem cells and platelets. The current invention provides a method for concentrating both osteogenic (mesenchymal stem cells) and osteoinductive (platelets) elements of marrow, whereas, for example, Muschler (Muschler et al., 2002; U.S. Pat. Nos. 5,824,084 and 6,049,026) describes a method to concentrate only mesenchymal stem cells from marrow. When combined with an osteoconductive scaffold, a concentrated marrow suspension of both stem cells and platelets should result in better bone healing compared to a marrow concentrate containing only stem cells. Furthermore, the present invention results in a concentrated cellular suspension that can be delivered to a bone defect by syringe injection through a needle. This should allow for minimally invasive delivery of the cell concentrate to a bone defect. The invention described by Muschler requires the use of a non-injectable osteoconductive scaffold, which precludes delivery of the cell concentrate/scaffold to a bone defect via injection. In other embodiments, a minimally invasive delivery, such as via syringe injection, is utilized.

Thus, a cell concentrate, the novel preparation of which is provided herein, is used to accelerate bone healing in a variety of bone grafting applications. Kits are also provided.

In one step of the present invention, the physiological solution is obtained, such as from an individual to which it will subsequently be delivered following concentration, and it is subjected to at least one filtration step, which may be a first filtration step in a process comprising more than one filtration steps, that selectively recovers or isolates nucleated cells, which comprise osteogenic cells, such as mesenchymal stem cells, and leukocytes; and platelets, which secrete osteoinductive growth factors, such as the exemplary PDGF, TGF-β, insulin-like growth factor-I (IGF-I), insulin-like growth factor-II (IGF-II), and vascular endothelial growth factor (VEGF), or mixtures thereof. Certain non-osteogenic components, such as red blood cells and plasma, which make up a large percentage of the sample volume, are not substantially recovered during the sole (or first) filtration step.

In one embodiment of the present invention, the blood or bone marrow fraction to be concentrated comprises an anticoagulant, provided preferably at the time of withdrawal, generally using an exemplary citrate-based anticoagulant. Any citrate-based anticoagulant is suitable, for example. Standard donor blood collection bags, for example, contain citrate-based anticoagulants. In a particular embodiment, the anticoagulant heparin is added, such as, for example, when bone marrow aspirate is used.

In particular embodiments, the physiological solution, such as the blood or bone marrow, comprises an additional component, such as another solution that acts as a diluent and/or source of hypotonicity. In the embodiment wherein the additional component is a hypotonic solution, upon introducing it to the physiological solution the salt concentration thereby becomes lower outside the cells comprised in the physiological solution than the salt concentration inside the cells. Thus, an osmotic gradient is generated wherein water flows into the cells, and, in specific embodiments, causes them to swell such that they adhere better to the filter. This solution, which may be referred to as Solution A in the Examples, may be, for example, water or a hypotonic sodium chloride solution that is less concentrated than isotonic (normal), which is, for example, about 0.9%.

Depending on the configuration of the one or more filters, the sole or first filter (a leukocyte reduction filter, in some embodiments) utilizes the tendency of certain types of cells (e.g., mesenchymal stem cells) to adhere to foreign substances. When passed through the filter, nucleated cells, such as stem cells, and platelets are adsorbed on the fiber surfaces within the filter, whereas red blood cells and plasma do not adsorb, and consequently pass through the filter. A purge solution, which may also be referred to as a recovery solution, is then flushed through the filter to remove the entrapped cells, thereby allowing recovery of the selected osteogenic/osteoinductive cells. These cells may then be analyzed and/or be applied to a wound site (such as a bone defect), optionally combined with a scaffold material before being applied to a wound site, or further processed. The recovery solution may in some embodiments be hypertonic or isotonic, such that they are equal or greater than normal saline concerning sodium chloride concentration.

In other embodiments, the recovered osteogenic/osteoinductive cells are then subjected to a second filtration step, wherein the platelets are increased in concentration. The filtration device of this step may be of any kind, so long as it concentrates nucleated cells, platelets, or both. In preferred embodiments, this step comprises subjecting the solution obtained from the first step to a hollow filtration device, such as those known in the art. The device preferably separates cells from a portion of the liquid in which they are suspended, thereby increasing the cellular concentration. A skilled artisan recognizes that the process is beneficial to the individual, given that a greater amount of therapeutic material may be delivered in a significantly smaller volume. In many embodiments, without such concentration of product, such a large volume would be prohibitive to apply to the defect. This second step may be performed multiple times.

In preferred embodiments, the second filtration device comprises a tubular filter, as opposed to a disk filter. In additional specific embodiments, the tubular filter is housed in an outer tube comprising hollow tubes within it and, in preferred embodiments, the flow through the tubular filtration device is parallel to the flow through the tubes within the tubular filtration device. In a specific embodiments, the pore size on the walls of the tubes is about 0.05 µm to about 5 µm, is more preferably about 0.1 µm to about 1 µm, and is most preferably about 0.2 µm to 0.5 µm.

In some embodiments of the present invention, the osteogenic cell concentrate is combined with a scaffold material and delivered to a bone defect. Any delivery method is appropriate as long as it maintains the integrity of the composition and provides therapy for the bone defect. The delivery method may be via syringe, scoop, spatula, scoopula, rod, tube, and so forth. In other embodiments, a viscous setting material is added to the osteogenic concentrate or to the osteogenic concentrate/scaffold material composition to facilitate retention of the concentrate or concentrate/scaffold mixture at the bone defect site. The viscous setting material may comprise a clotting factor (such as calcium, thrombin, or mixture thereof), bone marrow aspirate, blood, platelet rich plasma, fibrinogen/thrombin, a cement, a slurry, a paste, a combination thereof, and the like. In a specific embodiment, a cement, slurry, or paste, such as one or more comprising a calcium salt including calcium sulfate and/or calcium phosphate, is utilized in the present invention, such as for the viscous setting material.

Any of the surfaces of the filtration devices used in the present invention that contact a physiological solution and/or the resulting concentrate are preferably inert to the components and are preferably not substantially cytotoxic. In preferred embodiments, for example, where it is desirable to include cells such as nucleated cells and/or platelets concentrate, the contact surfaces are substantially noncytotoxic. Suitable materials include polycarbonates, polyurethane, acrylics, ABS polymers, polysolfone, polyethersulfone, mixed cellulose ester, polyester, and the like.

In embodiments wherein the sterility of the osteogenic concentrate or other composition must be maintained, as in the preparation of the concentrate for a bone defect therapy, any filtration surface that contacts any of the relevant compositions and/or the concentrate is preferably sterile or readily sterilizable. Commercially available filtration units can be sterilized by treating with agents such as gamma irradiation, ethylene oxide, formalin, hydrogen peroxide, sodium hypochlorite, heat, steam, and so forth. Sterile filtration units are commercially available for hematologic uses. Syringes and other fluid delivery systems are generally commercially available in sterile form as are various valves and stopcocks that are designed to attach to syringes and other blood processing products.

In alternative embodiments of the present invention, a bone marrow concentrate is generated by the methods described herein. The bone marrow concentrate is then utilized for an application other than a bone defect, such as for use in or augmentation of a bone marrow transplant.

Alternatively, the cell concentrate comprising or consisting essentially of platelets and nucleated cells but not plasma or red blood cells is not prepared at the point of care, such as being obtained as a commercially prepared composition or being prepared from an individual prior to a point of care service and administered to a bone defect of the same individual or another individual thereafter.

In particular embodiments of the present invention, there is a cell concentrate prepared by a method described herein.

III. Specific Embodiments

The previous discussion was directed to the general embodiments of the processes described herein. The following section provides specific embodiments to the procedures, although one of skill in the art would be able to make adjustments to the following steps for optimization of a method for concentrating a product. For example, these specific embodiments may be directed to processing from whole blood, and a skilled artisan recognizes which modifications would be helpful to optimize this method.

In a general embodiment of the present invention, a single step filtration process concentrates the desired cells, said cells exemplified by nucleated cells and platelets, through their isolation from a starting solution, such as bone marrow, whole blood, or a mixture thereof. This filtration step thereby removes plasma and red blood cells from the desired cells. The resultant filtrate comprising the desired cells is applied to a bone defect, optionally in a composition also comprising a scaffold material. An exemplary schematic of this embodiment is illustrated in FIG. 1.

In one specific embodiment, the following steps are utilized in the method:

Step 1, Obtain bone marrow: An appropriate amount of bone marrow (approximately 5 cc or greater, such as for bone grafting applications) is obtained, such as, for example, is aspirated into a syringe filled with an equal or lesser volume of an isotonic saline and a suitable anti-coagulant (e.g., citrate-based or heparin-based). In some embodiments, the bone marrow is obtained by another process, such as commercial purchase. In other embodiments, whole blood is the primary source of the concentrate, and it is processed, such as mixed with a suitable volume of anti-coagulant (e.g., citrate-based or heparin-based), prior to subjection to the nucleated cell-reduction filter of the next step.

Step 2, Filtration of marrow aspirate through a nucleated cell (such as a leukocyte) reduction filter to selectively recover nucleated cells, such as mesenchymal stem cells, and platelets (FIG. 1): The marrow aspirate is injected into a housing device, such as the small collection bag 10. An in-line leukocyte reduction filter 12 is placed between the collection bag 10 and a second housing device, such as the drain bag 14. The marrow aspirate is gravity-fed through the nucleated cell reduction filter 12 into the drain bag 14. The nucleated cell/platelet fraction (containing mesenchymal stem cells and platelets) is trapped within the filter 12 while the remaining blood constituents pass through. A syringe 18 is then used to backflush the filter with a suitable volume (>about 5 ml) of a purge solution (e.g., Dextran 40 and albumin solution) to allow the recovery of the buffy coat cells in a second sterile syringe 16.

Figure 2:
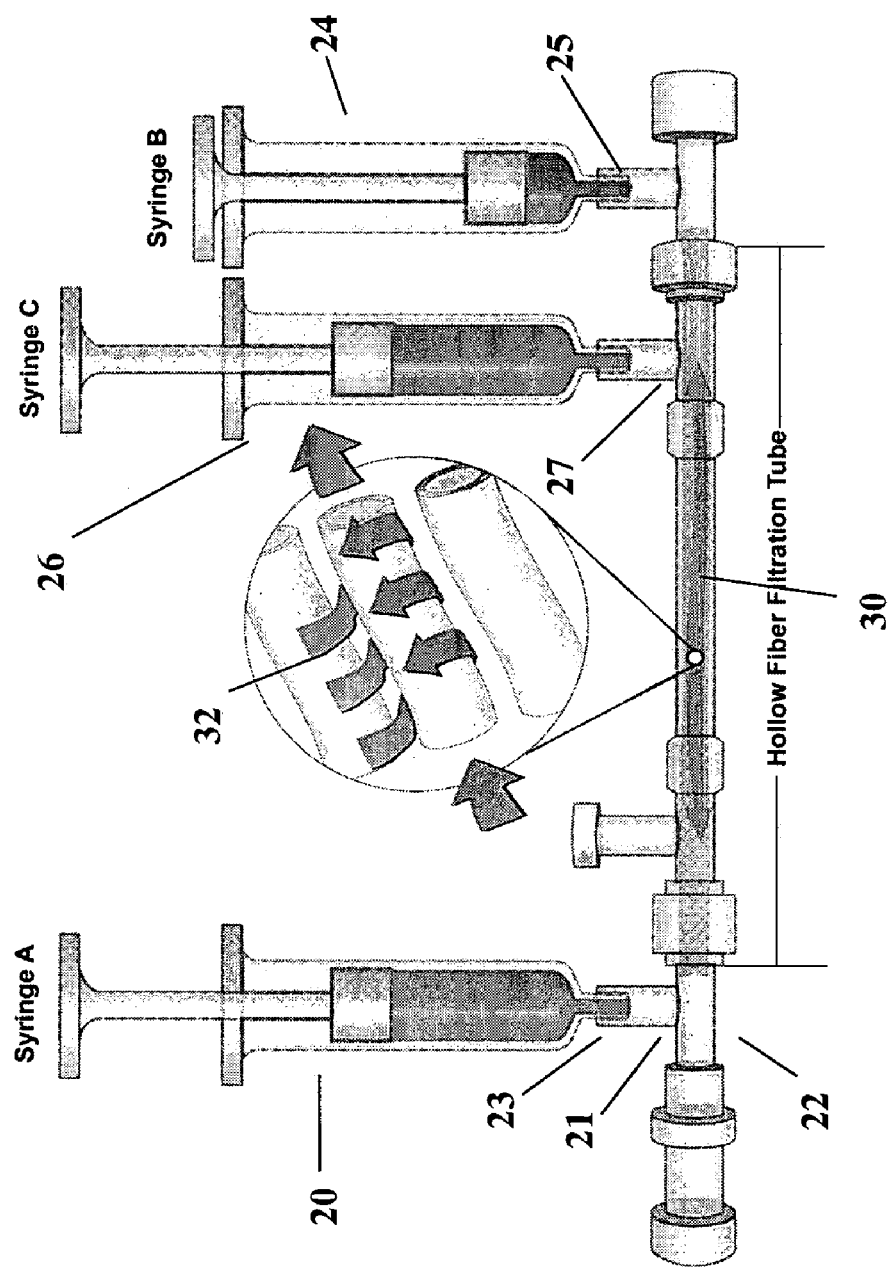
FIG. 2 provides a schematic showing an exemplary handheld operation of a hollow fiber filtration device.

Step 3, Filtration of cells suspended in purge solution through a hollow fiber filter to increase the concentration of the nucleated cells and platelets: The operation of the hollow fiber filtration device is shown schematically in FIG. 2. The syringe containing the cell-laden purge solution (labeled syringe A 20) is attached to one end of the filtration device 22, for example, by a Luer lock 23 at a first port 21. A second syringe (labeled syringe B 24) is attached to the opposing end through a second port 25 to collect the retenate (the cells that do not pass through the filter 30). A third syringe (labeled syringe C 26) is connected and is attached to a third port 27 to receive the filtrate (the liquid component, i.e., purge solution, that passes through the filter). The sample is passed back and forth between the two opposing retenate syringes (syringes A 20 and B 24) to allow circulation of the retenate and separation of the cellular and liquid components. The liquid component is passed through the semi-permeable filter membrane 30 into syringe C 26; cells cannot pass through the semi-permeable filter membrane 30 and are collected within the fibers 32 of the filter. In a specific embodiment, although other means are applicable, the following steps are performed in order to expel the cell concentrate from the filter 30 into a sterile syringe: (i) syringe C 26 is removed from the filtrate port 27 and the port 27 is capped; (ii) an empty retenate syringe (either A 20 or B 24) is removed from a retenate port (either 21 or 25, respectively); (iii) a syringe filled with a purge solution (preferably isotonic saline) is connected to the said available retenate port (either 21 or 25, respectively); and (iv) the purge solution, the volume of which is approximately equal to the priming volume of the filter 30, is injected into the filter 30 to expel the cell concentrate into the second retenate syringe (either A 20 or B 24, respectively).

Figure 3:
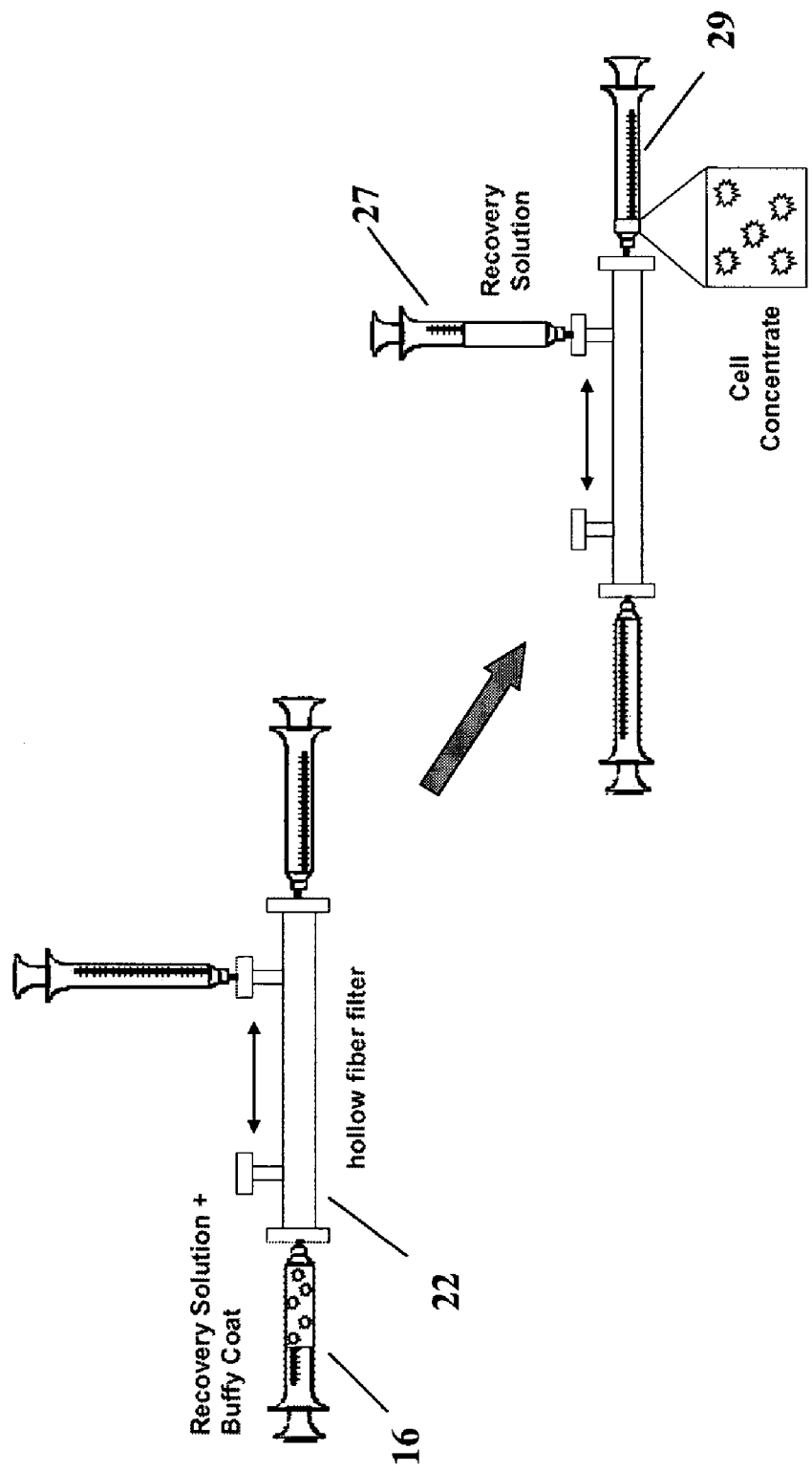
FIG. 3 illustrates a schematic showing the filtration of isolated nucleated cells and/or platelets through a hollow fiber filter to increase the concentration of the cells.

FIG. 3 illustrates a general embodiment showing that this filtration step fractionates the nucleated cell/platelet fraction and purge solution, thereby allowing the reduction of the volume of solution in which the cells are suspended. Again, a container 16 (which in some embodiments may be syringe A 20 or B 24 as described in FIG. 2) comprising the purge solution and buffy coat from the first filtration step delivers the solution to the hollow fiber filter 22, through which the solution is filtered. Ultimately, the purge solution will reside in a container 27, such as the illustrative syringe, and the desired cell concentrate is delivered to a container 29, such as the illustrative syringe, for eventual delivery to a defect. Thus, the net effect is an increase in the number of cells per unit volume of fluid.

Step 4, Mixing of cell concentrate with scaffold material: The concentrated cellular suspension is injected into a container holding a scaffold material, such as a granular material. In some embodiments, a variety of scaffold materials are used. The concentrate flows into the free space within and/or between individual scaffold granules. If the free volume available exceeds that of the cellular concentrate, then a carrier material (wherein the carrier material acts as a handling agent, acts to increase differentiation of mesenchymal cells towards an osteoblastic lineage, or both) may be mixed with the cell concentrate to achieve a volume that is equivalent to fill the free intergranular and/or intragranular space of the scaffold material. Examples of carrier materials include bio-fluids, such as coagulated blood, marrow, platelet-rich plasma, or a synthetic material, such as a hydrogel, powder, or granules. The cell concentrate may be combined with the carrier material by syringe mixing or by mixing in a container, using a rod, spatula, or other suitable instrument. The mixture is then injected into a container holding the granular scaffold material and allowed to flow into the intragranular and/or intergranular space. The cell concentrate/scaffold mixture can be delivered to an exposed defect or can be delivered percutaneously via syringe.

Whole blood (rather than marrow aspirate) could be processed in a similar manner as described in the previous embodiment. The resulting concentrate would be rich in platelets (but not mesenchymal stem cells) and could be mixed with a scaffold material as described in the previous embodiment.

A combination of bone marrow and blood could also be processed as described in the first embodiment. The resulting concentrate would be rich in both platelets and mesenchymal stem cells and could be mixed with a scaffold material as described in the first embodiment.

In a specific embodiment, following delivery of a cell concentrate/scaffold material mixture to a bone defect, the defect and/or the bone or bone tissue it is comprised in is tested. For example, the bone may be tested for quantity and/or quality of the bone, such as at the bone defect. The tests may comprise assaying bone density, strength, rate of bone formation, quality of bone, and so forth. Any suitable test may be utilized, and, in some embodiments, histology, radiographs and/or mechanical tests are employed. The percentage of the bone defect filled with bone following delivery of the cell concentrate/scaffold material mixture may be assayed, and, in some embodiments, it is compared to surrounding bone. In some embodiments, there is a test for increased deposition of calcium following administration of concentrate or concentrate/scaffold mixture.

In particular embodiments, a bone marrow aspirate is obtained for processing through a method described herein. Although bone marrow aspirate may be obtained by other means, a specific marrow aspiration technique is described: following induction of anesthesia and sterile skin preparation, a small incision (less than about 1 cm) is made along the posterior iliac crest. A bone marrow aspiration needle is advanced through this incision into the intramedullary cavity of the iliac crest. A small sample of bone marrow (less than about 4 mL) should be aspirated into a 10-mL syringe containing heparinized saline (about 1000 units/mL). After collection of marrow, the syringe is inverted several times to ensure mixing with the anticoagulant. Additional aspirations can be taken using the same technique through separate cortical perforations spaced at least about 1 cm apart.

In particular embodiments, blood is obtained for processing through a method described herein. Although blood may be obtained by other means, a specific blood aspiration step is described: following sterile skin preparation, a small needle (18-21 gauge) infusion set is used to draw blood from a suitable large peripheral vein, typically the antecubital or cephalic vein. Blood is drawn into a 60 cc syringe filled with citrate anticoagulant at a ratio of approximately 10:1 (blood: anticoagulant). After collection of blood, the syringe is inverted several times to ensure mixing with the anticoagulant.

IV. Apparatuses

An apparatus of the present invention or one that is utilized in a method of the present invention may comprise at least one filtration component. One or more filters may be utilized in the apparatus or a component thereof. A filter may be designed to utilize "cross-flow filtration" or "cross-flow mode" in which there is recirculation of a retentate across the surface of the membrane filter. In alternative embodiments, a filter is designed to utilize "dead-end filtration" or "dead-end mode", which refers to having substantially no tangential flow filtration.

Microfiltration may be utilized in the invention, which regards separation of particles from a fluid. At least one microfiltration device comprises at least one filter having a pore size of about 0.05 μm to about 5 μm. In a specific embodiment of the present invention, cells and/or cell fragments are separated from at least some fluid, wherein the microfiltration capabilities of the filter permit passage of the fluid through the pores, thereby retaining the cells and/or cell fragments.

A filtration device may be of any kind, so long as it concentrates nucleated cells, platelets, or both. In preferred embodiments, a device preferably separates cells from a portion of the liquid in which they are suspended, thereby increasing the cellular concentration.

In preferred embodiments, a filtration device may comprise a tubular filter, as opposed to a disk filter. In additional specific embodiments, the tubular filter is housed in an outer tube comprising hollow tubes within it and, in preferred embodiments, the flow through the tubular filtration device is parallel to the flow through the tubes within the tubular filtration device. In a specific embodiments, the pore size on the walls of the tubes is about 0.05 μm to about 5 μm, is more preferably about 0.1 μm to about 1 μm, and is most preferably about 0.2 μm to 0.5 μm.

In some embodiments of the present invention, a hollow fiber filtration device is utilized and may be commercially obtained. The device comprises, in particular embodiments, a hollow tubular outer covering, wherein inside the hollow tubular outer covering there are individual tubes whose walls are filters; the individual tubes lay in a direction parallel to the length of the tube. In specific embodiments, the direction of feed of a product through a device is perpendicular to the direction of flow across the membrane. In some embodiments it generally comprises tangential flow filtration, which regards the recirculation of a retentate across the surface of the membrane filter. In alternative embodiments, there is no tangential flow filtration.

A skilled artisan recognizes that any filtration surface that contacts any of the relevant compositions and/or the concentrate is preferably sterile or readily sterilizable. Commercially available filtration units can be sterilized by treating with agents such as gamma irradiation, ethylene oxide, formalin, hydrogen peroxide, or sodium hypochlorite. Sterile filtration units are commercially available for hematologic uses. Syringes and other fluid delivery systems are generally commercially available in sterile form as are various valves and stopcocks that are designed to attach to syringes and other blood processing products.

An apparatus utilized in methods described herein may be considered disposable, although they may be reused upon sterilization, such as by gamma sterilization. Filters and syringes may be commercially obtained. In a specific embodiment, the apparatus is plastic. In further specific embodiments, the footprint of the leukoreduction filter is approximately 12 cm in diameter and 25 mm thick and/or the footprint of the hollow fiber filter is approximately 120 mm long×20 mm.

V. Addition of Biological Agents to the System

In a preferred embodiment of the present invention a biological agent is included in the material delivered to the bone defect (either the cell concentrate, the scaffold material, or both). Examples include antibiotics, growth factors, fibrin, bone morphogenetic factors, bone growth agents, chemotherapeutics, pain killers, bisphosphonates, strontium salt, fluoride salt, magnesium salt, and sodium salt.

In contrast to administering high doses of antibiotic orally to an organism, the present invention allows antibiotics to be included within the material of the composition for a local administration. This reduces the amount of antibiotic required for treatment of or prophalaxis for an infection. Administration of the antibiotic by the material in a composition would also allow less diffusing of the antibiotic, particularly if the antibiotic is contained within a fibrin matrix. Alternatively, the scaffold material of the present invention may be coated with the antibiotic and/or contained within the scaffold material or the concentrate, or a combination thereof. Examples of antibiotics are tetracycline hydrochloride, vancomycin, cephalosporins, and aminoglycocides such as tobramycin and gentamicin, and quinolone antibiotics, such as ciprofloxacin.

Growth factors may be included in the material for a local application to encourage bone growth. Examples of growth factors that may be included are platelet derived growth factor (PDGF), transforming growth factor β (TGF-β), insulin-like growth factor-I (IGF-I), insulin-like growth factor-II (IGF-II), fibroblast growth factor (FGF), beta-2-microglobulin (BDGF II), bone morphogenetic protein (BMP), growth and differentiation factor-5 (GDF-5), vascular endothelial growth factor (VEGF), or mixtures thereof. The scaffold material of the present invention may be coated with a growth factor and/or contained within the scaffold material or the concetrate, or a combination thereof.

Proteins or agents which are accessory to and/or bind to growth factor may be used in the present invention. Examples of the growth factor binding/accessory protein includes follistatin, osteonectin, sog, chordin, dan, cyr61, thrombospondin, type IIa collagen, endoglin, cp12, nell, crim, acid-1 glycoprotein, and alpha-2HS glycoprotein.

In some embodiments, the compositions of the present invention include a cell, such as an osteoblast, endothelial cell, fibroblast, adipocyte, myoblast, mesenchymal stem cell, chondrocyte, multipotent stem cell, pluripotent stem cell and totipotent stem cell, or a musculoskeletal progenitor cell.

Bone morphogenetic factors may include growth factors whose activity is specific to osseous tissue including proteins of demineralized bone, or DBM (demineralized bone matrix), and in particular the proteins called BP (bone protein) or BMP (bone morphogenetic protein), which actually contains a plurality of constituents such as osteonectin, osteocalcin and osteogenin. The factors may coat the scaffold material of the present invention and/or may be contained within the scaffold material, the concentrate, or a combination thereof.

Angiogenic factors may be included on the scaffold material or in the scaffold material or concentrate, or a combination thereof. Some examples of angiogenic factors include monobutyrin, dibutyrin, tributyrin, butyric acid, vascular endothelial growth factor (VEGF), erucimide, thymosin Beta 4(TB4), synthetic peptide analogs to heparin binding proteins, nicotine, nicotinamide, spermine, angiogenic lipids, ascorbic acid and derivatives thereof and thrombin, including analogs and peptide fragments thereof.

Bone growth agents may be included within the scaffold material, concentrate, or both, of the composition of the invention, in a specific embodiment. For instance, nucleic acid sequences that encode an amino acid sequence, or an amino acid sequence itself may be included in the concentrate and/or scaffold material of the present invention wherein the amino acid sequence facilitates bone growth or bone healing. As an example, leptin is known to inhibit bone formation (Ducy et al., 2000). Any nucleic acid or amino acid sequence that negatively impacts leptin, a leptin ortholog, or a leptin receptor may be included in the composition. As a specific example, antisense leptin nucleic acid may be transferred within the composition of the invention to the site of a bone deficiency to inhibit leptin amino acid formation, thereby avoiding any inhibitory effects leptin may have on bone regeneration or growth. Another example is a leptin antagonist or leptin receptor antagonist.

The nucleic acid sequence may be delivered within a nucleic acid vector wherein the vector is contained within a delivery vehicle. An example of such a delivery vehicle is a liposome, a lipid or a cell. In a specific embodiment the nucleic acid is transferred by carrier-assisted lipofection (Subramanian et al., 1999) to facilitate delivery. In this method, a cationic peptide is attached to an M9 amino acid sequence and the cation binds the negatively charged nucleic acid. Then, M9 binds to a nuclear transport protein, such as transportin, and the entire DNA/protein complex can cross a membrane of a cell.

An amino acid sequence may be delivered within a delivery vehicle. An example of such a delivery vehicle is a liposome. Delivery of an amino acid sequence may utilize a protein transduction domain, an example being the HIV virus TAT protein (Schwarze et al., 1999).

In a preferred embodiment the biological agent of the present invention has high affinity for a fibrin matrix.

In a specific embodiment, the particle of the present invention may contain within it or on it a biological agent which would either elute from the particle as it degrades or through diffusion.

The biological agent may be a pain killer. Examples of such a pain killer are lidocaine hydrochloride, bipivacaine hydrochloride, and non-steroidal anti-inflammatory drugs such as ketorolac tromethamine.

Other biological agents that may be included in the suspension material or contained on or in the concentrate and/or scaffold material of the present invention are chemotherapeutics such as cis-platinum, ifosfamide, methotrexate and doxorubicin hydrochloride. A skilled artisan is aware which chemotherapeutics would be suitable for a bone malignancy.

Another biological agent which may be included in the concentrate and/or scaffold material is a bisphosphonate. Examples of bisphosphonates are alendronate, clodronate, etidronate, ibandronate, (3-amino-1-hydroxypropylidene)-1, 1-bisphosphonate (APD), zoledronate, dichloromethylene bisphosphonate, aminobisphosphonatezolendronate and pamidronate.

The biological agent may be either in purified form, partially purified form, commercially available or in a preferred embodiment are recombinant in form. It is preferred to have the agent free of impurities or contaminants.

VI. Combined Therapy

A skilled artisan recognizes that the present invention provided herein in some embodiments is used in conjunction with another therapy for the individual. For example, in the embodiments wherein a bone defect is being treated with methods and/or compositions of the present invention, the patient may also receive standard bone therapy treatments. Standard bone therapy treatments for repair of bone defect include surgery, additional bone grafting, antibiotic administration, implant use, external stimulation such as low-intensity ultrasound or electromagnetic pulses, and so forth.

VII. Pharmaceutical Compositions and Routes of Administration

Compositions of the present invention will have an effective amount of an osteogenic material for therapeutic administration. In some embodiments, the compositions are used in combination with an effective amount of a second compound (second agent) that is a bone therapy agent as exemplified above. Such compositions will generally be dissolved or dispersed in a pharmaceutically acceptable carrier or aqueous medium. The term "effective" as used herein refers to providing bone growth properties, preventing degeneration, strengthening of bone, preventing fracture, healing fracture, and so forth.

The phrases "pharmaceutically or pharmacologically acceptable" refer to molecular entities and compositions that do not produce an adverse, allergic or other untoward reaction when administered to an animal, or human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredients, its use in the therapeutic compositions is contemplated. Supplementary active ingredients, such as other bone therapy agents, can also be incorporated into the compositions.

The compositions of the present invention are advantageously administered in a form suitable for application to a bone defect. The composition form may be injectable compositions, either as liquid solutions or suspensions, although solid forms suitable for solution in, or suspension in, liquid prior to injection also may be prepared. In other embodiments, the composition is applied in a non-injectable manner. Examples of such include applying a cell concentrate alone or in a mixture with a scaffold material using a utensil, such as a scoop, scoopula, spatula, rod, spoon, syringe, pipette, forceps, measured spoon, or any such medically approved delivery vehicle.

In particular embodiments of the present invention, a solution comprising the desired cell concentrate comprises phosphate buffer, dextrose, salt, dextran 40, dextran 70, or a mixture or combination thereof. Other pharmaceutically acceptable carriers include aqueous solutions, non-toxic excipients, including salts, preservatives, buffers and the like. Examples of non-aqueous solvents are propylene glycol, polyethylene glycol, vegetable oil and injectable organic esters, such as theyloleate. Aqueous carriers include water, alcoholic/aqueous solutions, saline solutions, parenteral vehicles such as sodium chloride, Ringer's dextrose, etc. Preservatives include antimicrobial agents, anti-oxidants, chelating agents and inert gases, although in specific embodiments the concentrate is used soon after concentration at the point-of-care. The pH and exact concentration of the various components in the pharmaceutical are adjusted according to well-known parameters.

All of the essential materials and reagents required for bone therapy may be assembled together in a kit. When the components of the kit are provided in one or more liquid solutions, the liquid solution preferably is an aqueous solution, with a sterile aqueous solution being particularly preferred. In the kit, there may be an apparatus to collect a physiological solution, at least one filter and/or filter apparatus, a scaffold material, a utensil and/or platform to combine the cell concentrate and scaffold material, and/or a combination thereof.

The kits of the present invention also will typically include a means for containing the vials in close confinement for commercial sale such as, e.g., injection or blow-molded plastic containers into which the desired vials are retained. Irrespective of the number or type of containers, the kits of the invention also may comprise, or be packaged with, an instrument for assisting with the injection/administration or placement of the ultimate complex composition within the body of an animal. Such an instrument may be a scoop, scoopula, spatula, rod, spoon, syringe, pipette, forceps, measured spoon, or any such medically approved delivery vehicle.

The concentrate or concentrate/scaffold material can also be comprised with a solvent or dispersion medium comprising, for example, blood, plasma, water, sugar, salt, or suitable mixtures thereof. The prevention of the action of microorganisms can be brought about by various antibacterial and antifungal agents, for example, parabens, chlorobutanol, phenol, sorbic acid, thimerosal, and the like.

VIII. Kits

In some embodiments of the present invention, kits are provided, such as to perform methods described herein and/or generate compositions described herein. In a particular embodiment, these kits are utilized for treatment of a bone defect. In some particular embodiments, there is a kit for preparing a cell concentrate, comprising a first filtration device and a second filtration device, both of which are housed in a suitable container. The first filtration device may be a nucleated cell filtration device and/or the second filtration device is a microfiltration device, such as, for example, a hollow fiber filtration device.

The kit may further comprise a scaffold material housed in a suitable container. The kit may further comprise a biological agent housed in a suitable container. An exemplary biological agent includes a growth factor, an antibiotic, a strontium salt, a fluoride salt, a magnesium salt, a sodium salt, a bone morphogenetic factor, an angiogenic factor, a chemotherapeutic agent, a pain killer, a bisphosphonate, a growth factor binding/accessory protein, a cell, a bone growth agent, or a mixture thereof. In a specific embodiment, the growth factor is selected from the group consisting of platelet derived growth factor (PDGF), transforming growth factor β (TGF-β), insulin-related growth factor-I (IGF-I), insulin-related growth factor-II (IGF-II), fibroblast growth factor (FGF), beta-2-microglobulin (BDGF II), nerve growth factor (NGF), epidermal growth factor (EGF), keratinocyte growth factor (KGF), bone morphogenetic protein (BMP) and a mixture thereof. In a further specific embodiment, the antibiotic is selected from the group consisting of tetracycline hydrochloride, vancomycin, cephalosporins, quinolone, aminoglycocides, and a mixture thereof. In a specific embodiment, the quinolone is ciprofloxacin. In a specific embodiment, the aminoglycocide is tobramycin or gentamicin.

In other embodiments, there is a kit for treating a bone defect, comprising a plurality of cells housed in a suitable container, wherein the cells are nucleated cells, platelets, or both. Such a kit may comprise a scaffold material housed in a suitable container and/or a biological agent housed in a suitable container.

A kit may comprise an apparatus for the preparation of a cell concentrate obtained by a method or methods described herein. A kit of the present invention may comprise, at least, any apparatus suitable to perform any method described herein.

The kits provided herein may be considered single use disposable kits.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Dual Filtration of Physiological Solution

An in vitro study is performed to determine the efficacy of the filter device in concentrating nucleated cells, such as mesenchymal stem cells, and platelets within bone marrow aspirate, although in some embodiments blood or a mixture of blood and bone marrow may be utilized. A volume of the exemplary marrow aspirate, such as 25 mL, is procured from an animal donor(s) (such as, for example, sheep). Each sample is divided, wherein half the sample is not processed and half the sample is processed by the filtration device(s) described herein. The volume of the unprocessed sample (V0) and that of the sample after it has been processed (V1) is measured. Nucleated cell count, mesenchymal stem cell count, and platelet count is determined by hemocytometry and flow cytometry for each unprocessed and processed sample. Additionally, in order to quantify the concentration of mesenchymal stem cells that differentiate towards an osteoblastic lineage, cells from the unprocessed marrow and the cell concentrate are cultured in osteogenic media and assayed for osteoblastic markers, such as, for example, alkaline phosphatase. Nucleated cell count, platelet count, and alkaline phosphatase activity is normalized to sample volume (V0 or V1) to yield a measure of nucleated cell, mesenchymal stem cell, and platelet concentration. The filtration of the marrow aspirate should result in a significant retention of mesenchymal stem cells and platelets (preferably greater than about 60%) and a significant reduction in volume (preferably greater than about 80%) compared to unprocessed marrow. This should result in an approximately 3-fold or greater increase in cell concentration compared to unprocessed marrow aspirate.

In light of the demonstration of the efficacy of the filter device in concentrating marrow in vitro, an implantation study is performed to determine acceleration of bone healing by the concentrated marrow suspension in an animal model (such as, for example, sheep). Autologous marrow aspirate is processed through the filter instrument to increase the concentration of mesenchymal stem cells and platelets. The concentrated marrow suspension is combined with an osteoconductive scaffold material and, if necessary, a carrier material, and implanted in a critical-sized defect (such as, for example, a defect that will not spontaneously heal when left empty). The concentrated marrow aspirate+scaffold group is compared to an unprocessed marrow aspirate+scaffold group in terms of bone healing. Bone healing is measured radiographically, mechanically, and/or histologically by standard means in the art. The concentrated marrow aspirate group preferably shows superior bone healing compared to the unprocessed marrow aspirate group.

Example 2

Description of Exemplary Filter Configurations

Exemplary filter configurations in the present invention may be as follows:
1. Leukofilter only (see FIG. 4);
2. Leukofilter+Hollow Fiber Filter (Cross-flow mode) (see FIGS. 4, 5, 6);

3. Leukofilter+Hollow Fiber Filter (Dead end mode) (see FIGS. 4, 7, 8); and/or

Figure 9:
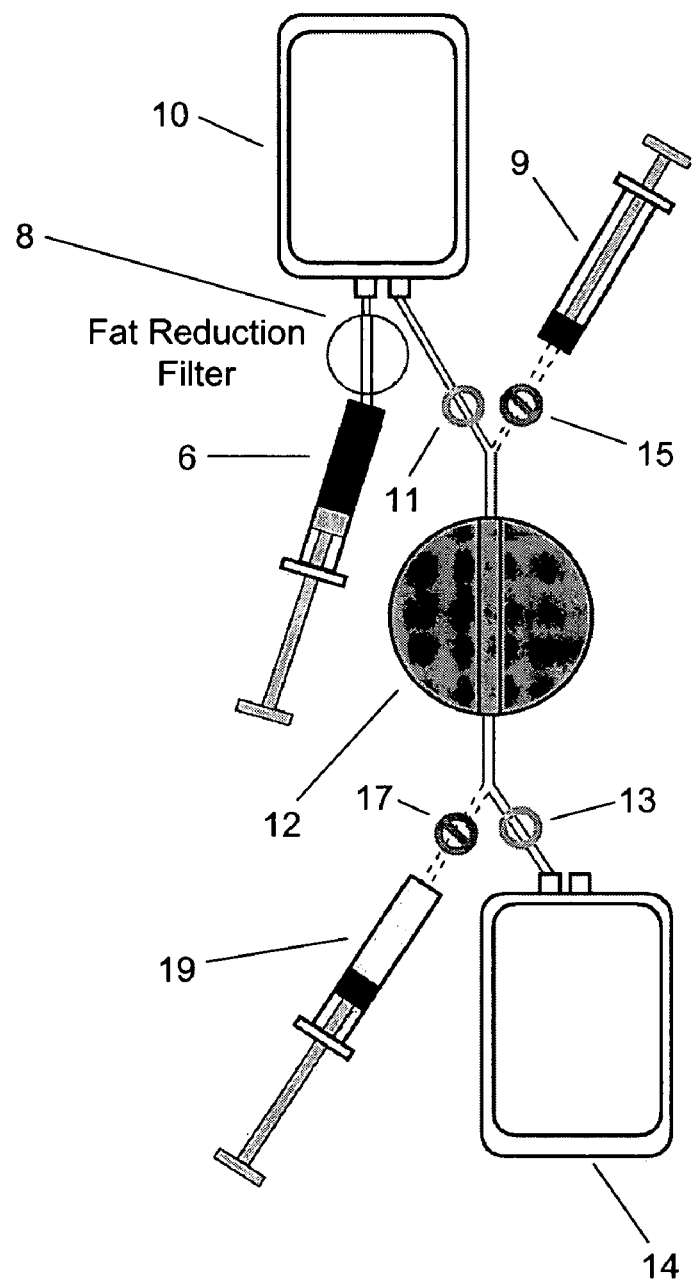
FIGS. 9A-9E provide an exemplary schematic showing operation of fat reduction filter to decrease fat particle content in physiological solution and a leukofilter to selectively recover osteogenic cells (i.e., platelets and nucleated cells) from said physiological solution.
Figure 9:
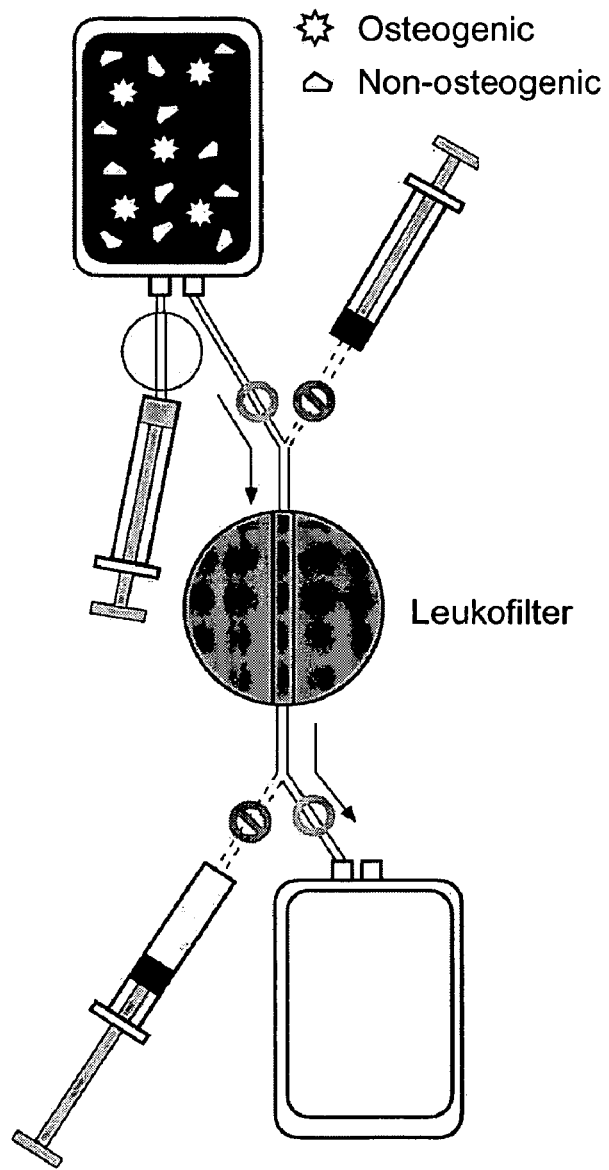
Figure 9:
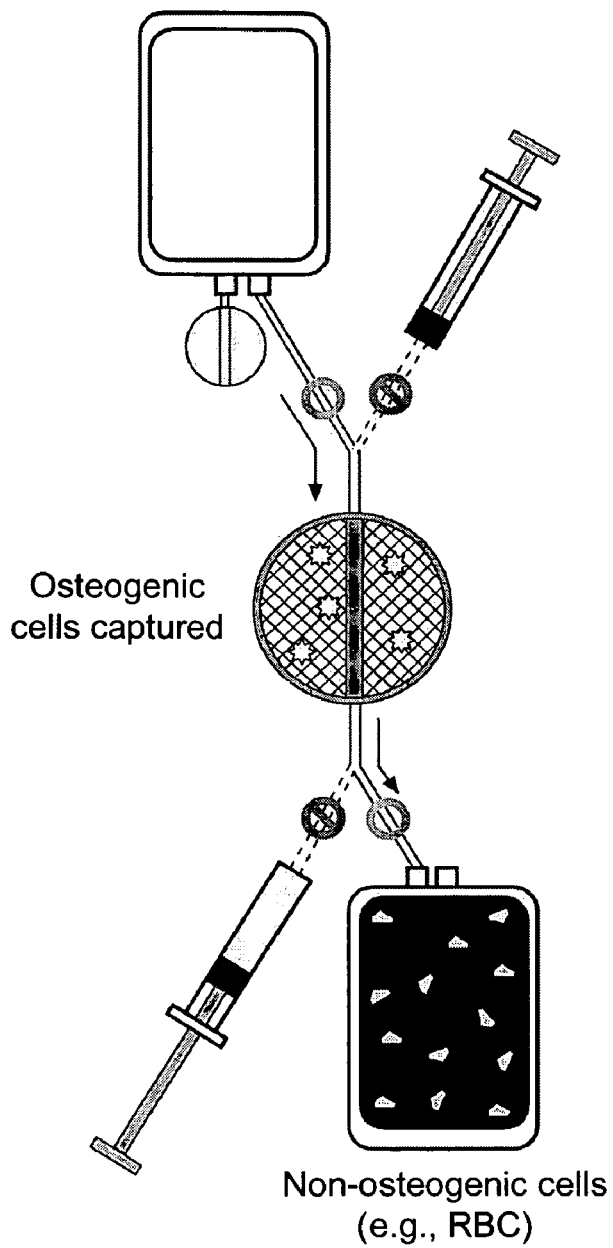
Figure 9:
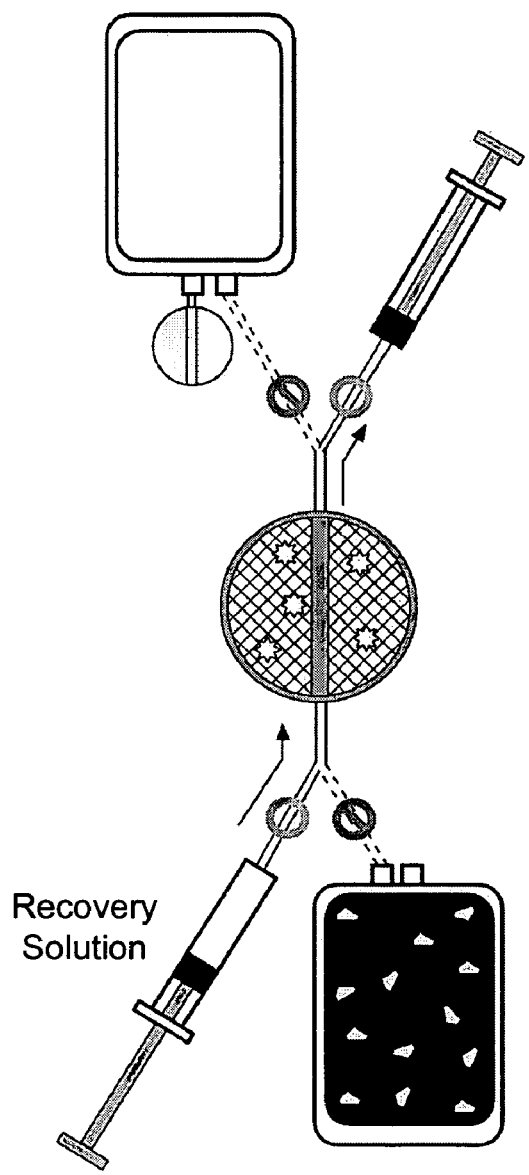
Figure 9:
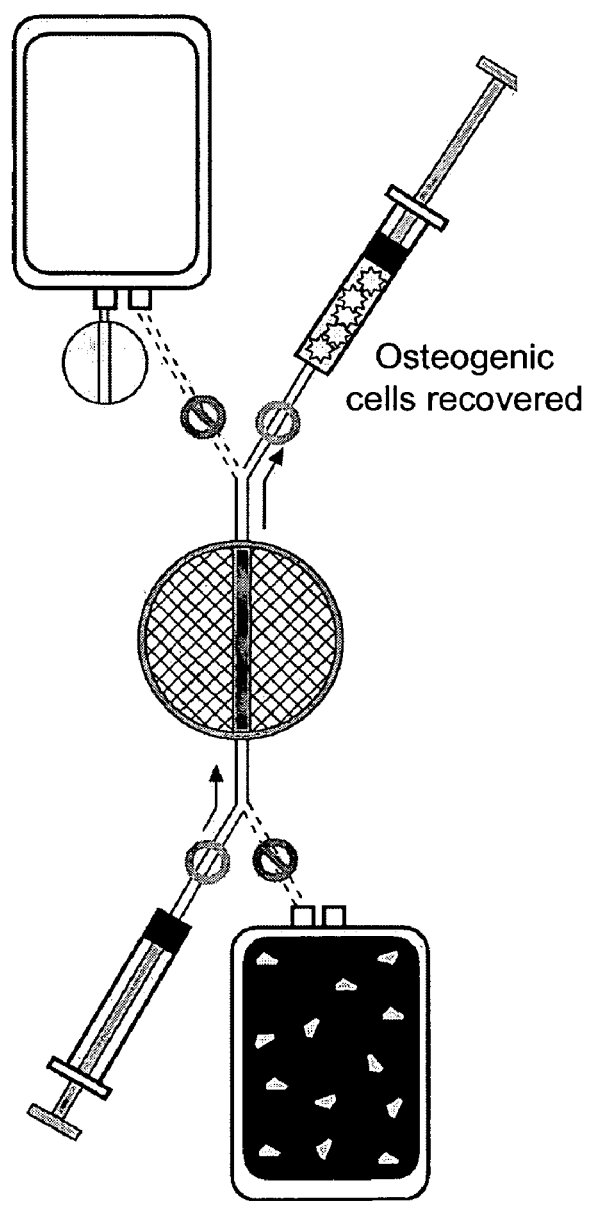
Figure 10:
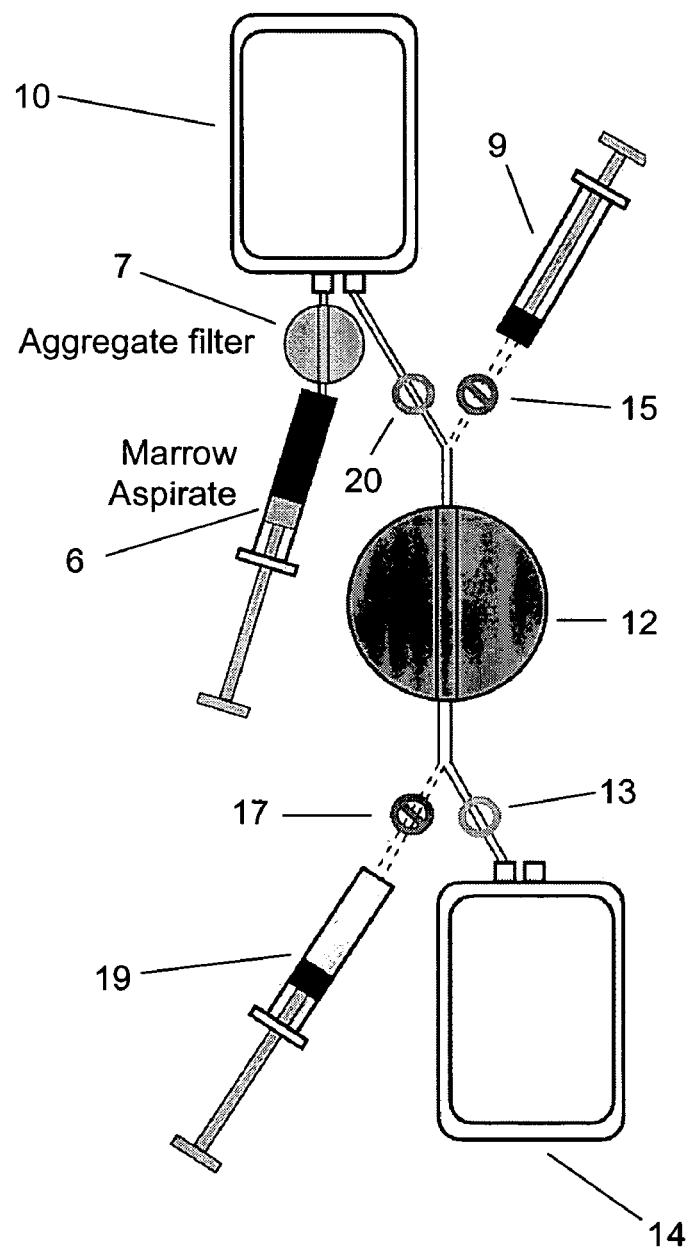
FIGS. 10A-10E illustrate a specific embodiment wherein the filtration process utilizes an aggregate filter, such as a cellular and/or non-cellular fat reduction filter.
Figure 10:
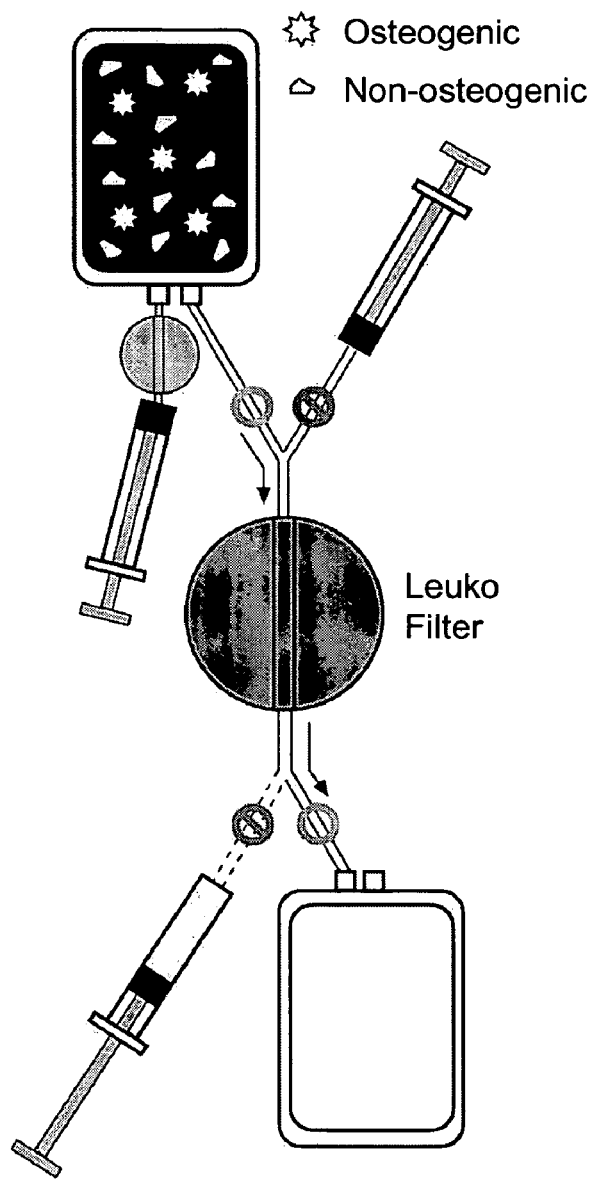
Figure 10:
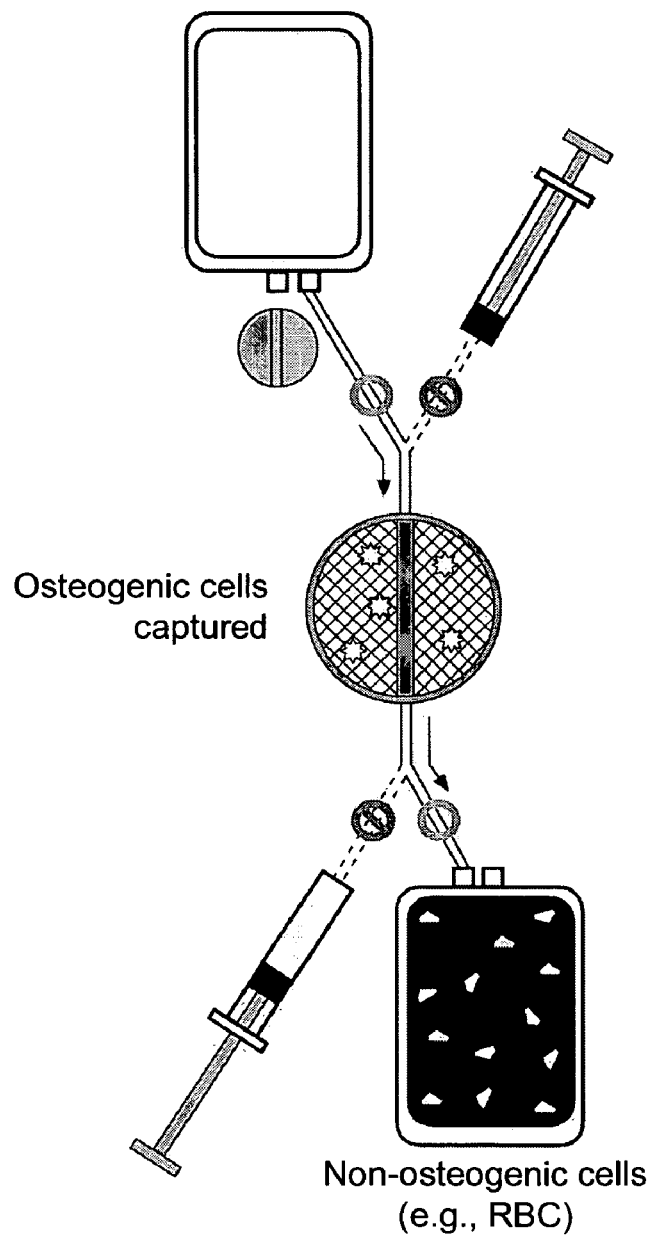
Figure 10:
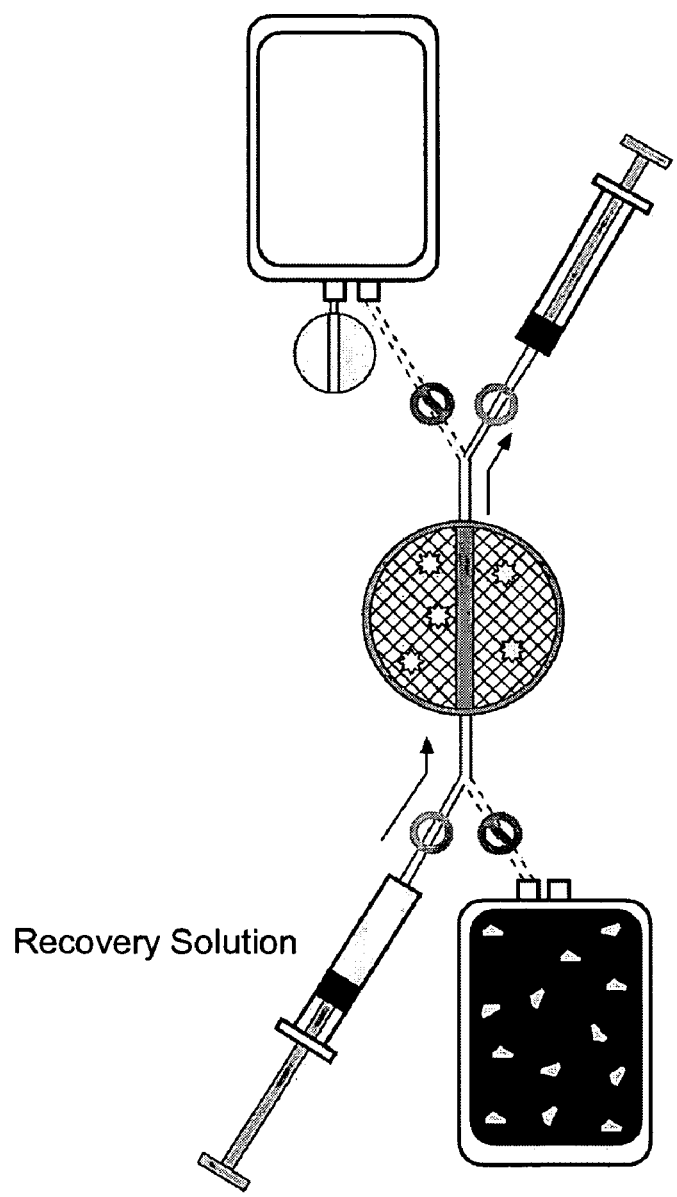
Figure 10:
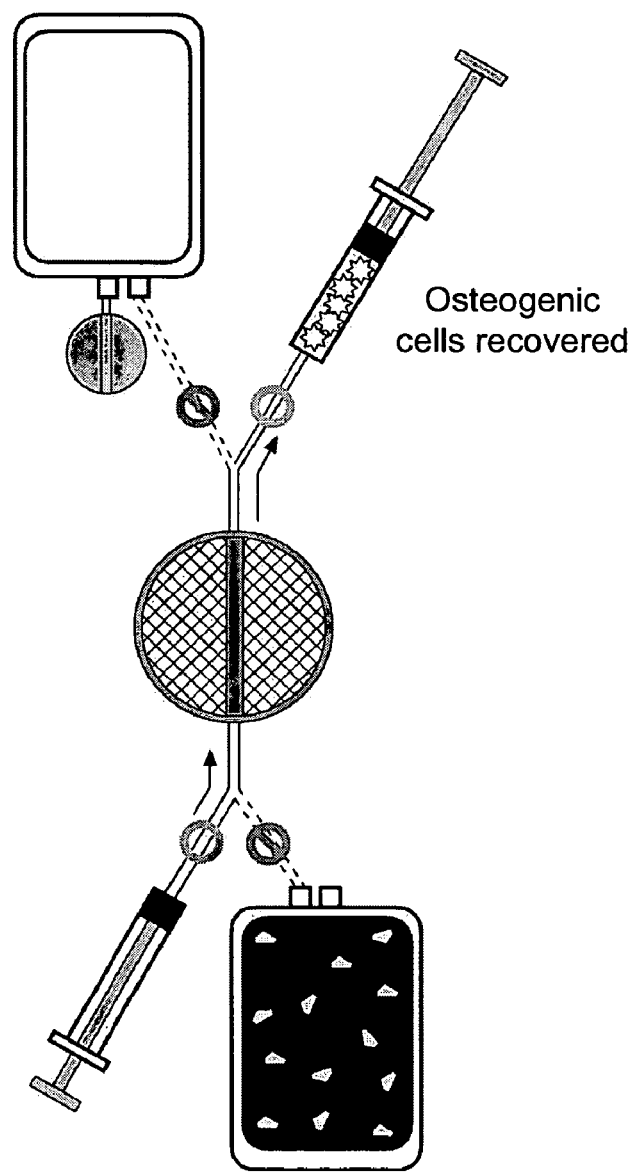

4. Use of a Fat Reduction Filter with any of the above three configurations (FIG. 9).

In FIGS. 4A-4D, there is a schematic showing operation of a sole (or first, as in some embodiments described below) filter (such as a leukocyte reduction-type filter), to selectively recover osteogenic cells (i.e. platelets and nucleated cells) from a physiological solution. In the Fill step (FIG. 4A), a physiological solution comprising both osteogenic and non-osteogenic cells and optionally comprising anticoagulant is injected into a collection bag 10. In a filtration step (FIG. 4B), the physiological solution passes from the collection bag 10 through the leukocyte reduction-type filter 12, such as by gravity feed. After passing through the filter where cells such as nucleated cells, platelets, or a mixture thereof are retained, the remainder of the physiological solution and its constituents (such as red blood cells) flow into the drain bag 14. In a back-flush step (FIG. 4C), valves 11 and 13 to the collection bag 10 and drain bag 14, respectively, are closed. The valves 15 and 17 to the syringes 9 and 19, respectively, are opened. In the recovery step (FIG. 4D), osteogenic cells are backflushed from the filter 12 when recovery solution from syringe 19 flows through valve 17 to force the osteogenic cells into syringe 9. The collection in syringe 9 comprises the recovered cells and in some embodiments is not processed further but is applied to a bone defect, optionally after combining the cells with a scaffold material. In alternative embodiments, the cells in syringe 9 are referred to as a feed for a subsequent step in the process, and the syringe may be referred to as a feed syringe 9.

Figure 4:
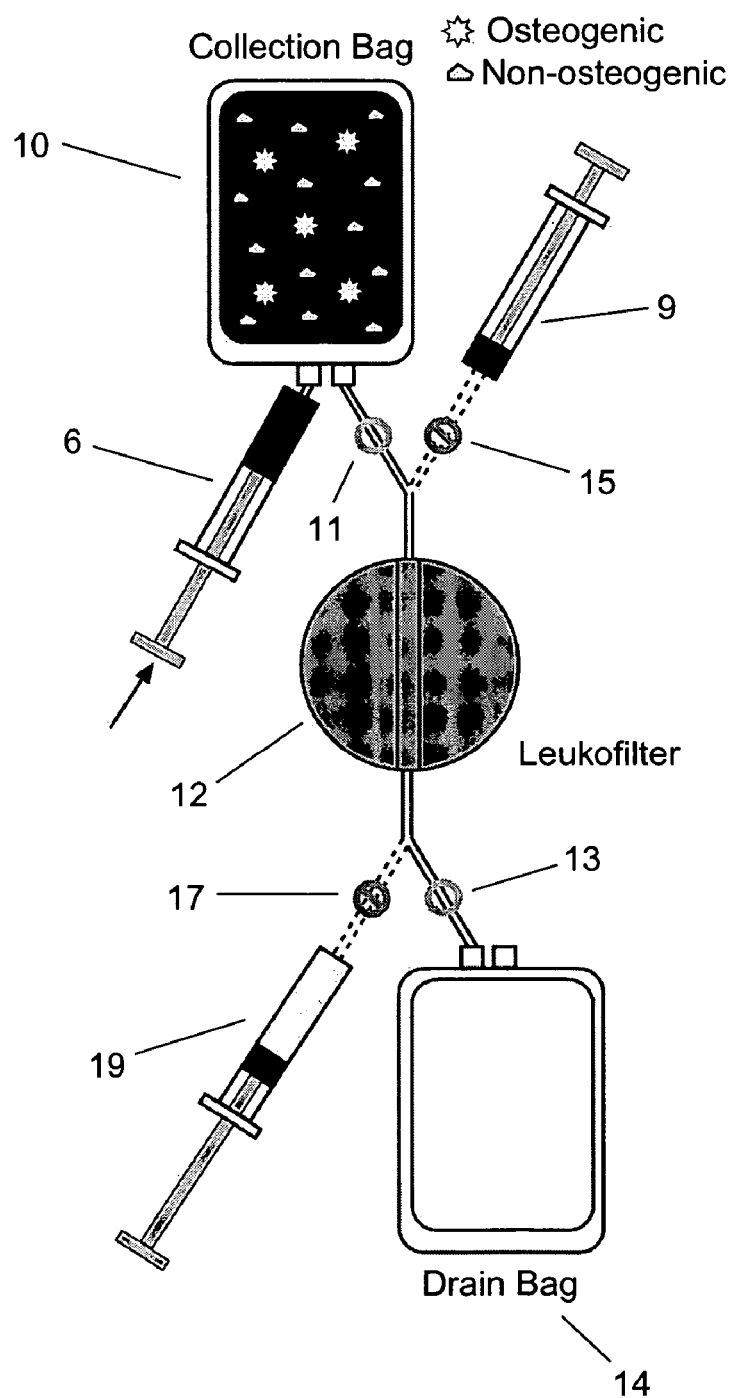
FIGS. 4A-4D provide an exemplary schematic showing operation of first filter (leukoreduction-type filter) to selectively recover osteogenic cells (i.e., platelets and nucleated cells) from a physiological solution.
Figure 4:
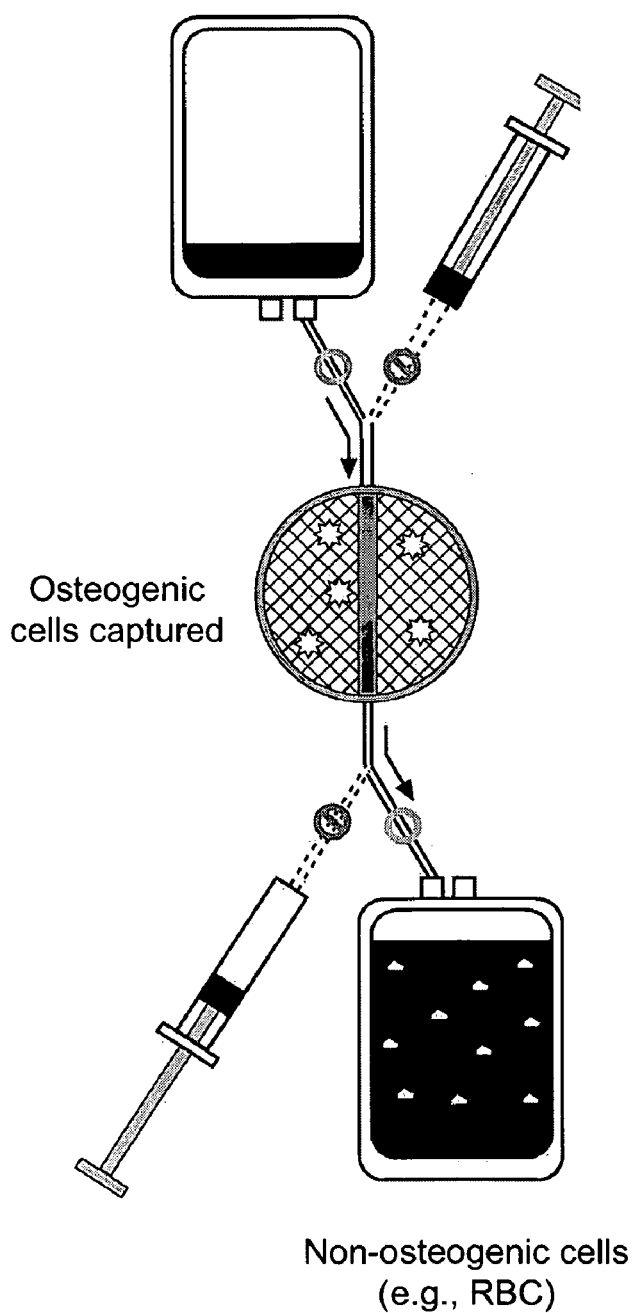
Figure 4:
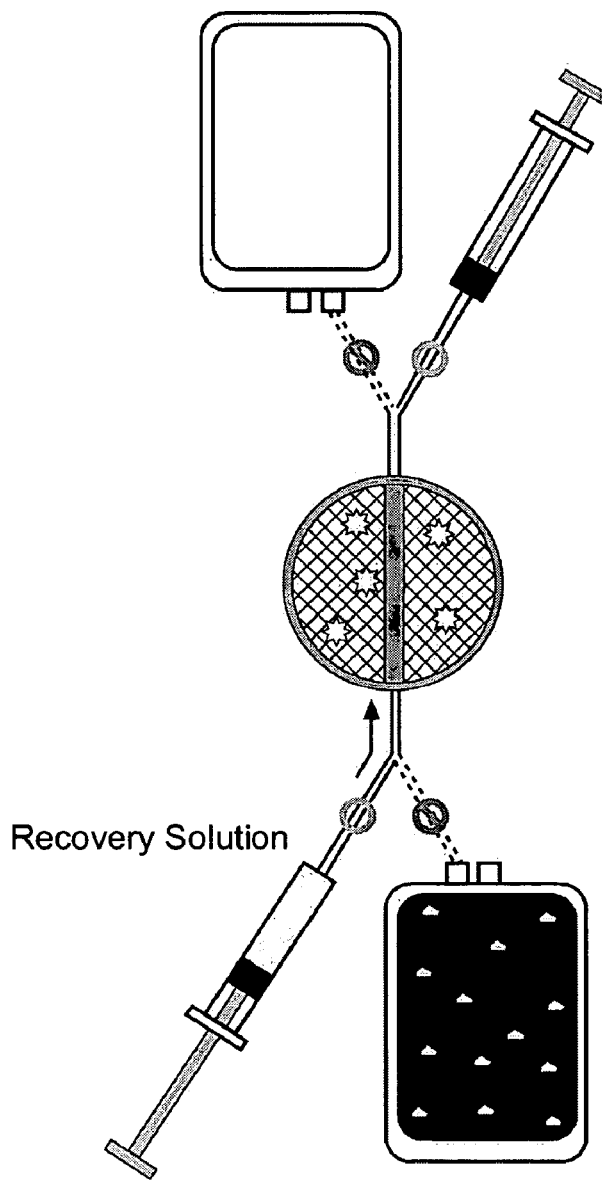
Figure 4:
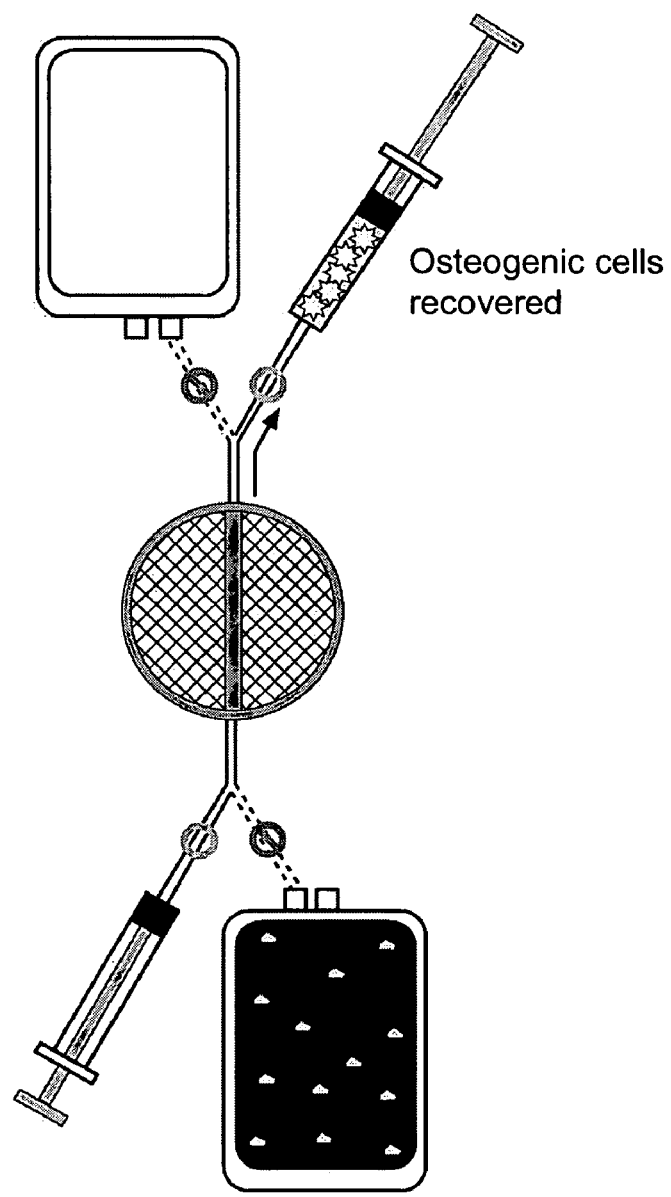
Figure 5:
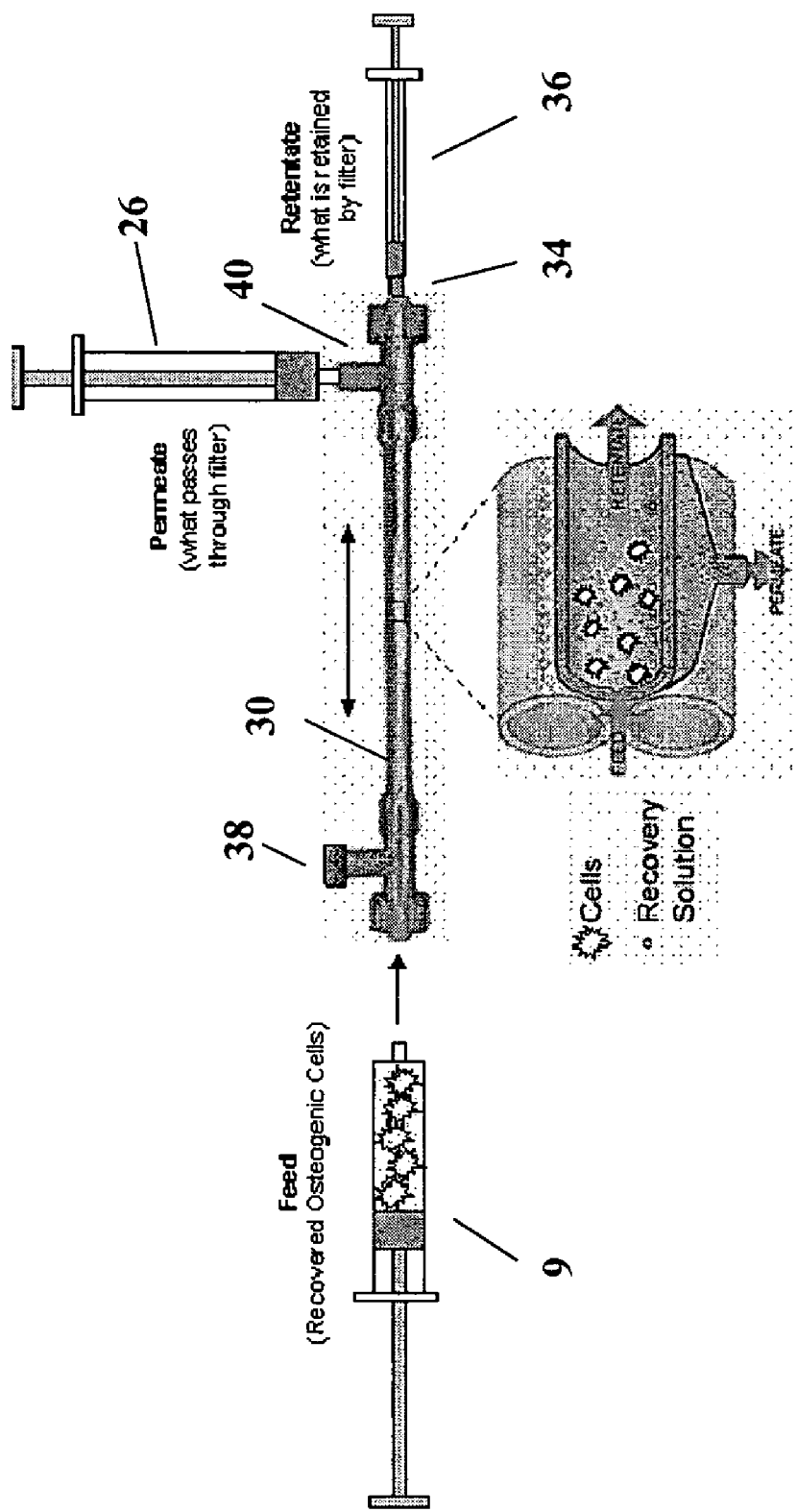
FIG. 5 illustrates an exemplary schematic showing operation of a second filter (hollow fiber filter) to concentrate osteogenic cells (i.e., platelets and nucleated cells) recovered from first filter. The syringe containing the recovered osteogenic cells is connected to the hollow-fiber filter, which is operated in cross-flow mode. In cross-flow filtration, the feed stream is recirculated between a feed syringe and retentate syringe tangentially to the membrane, establishing a pressure differential across the membrane. This causes some of the particles to pass through the membrane. Remaining particles continue to flow across the membrane. Using an appropriate membrane pore size (0.2 to 0.5 µm), recovery solution, but not cells, are able to pass through the filter membrane of the hollow fiber filter.
Figure 6:
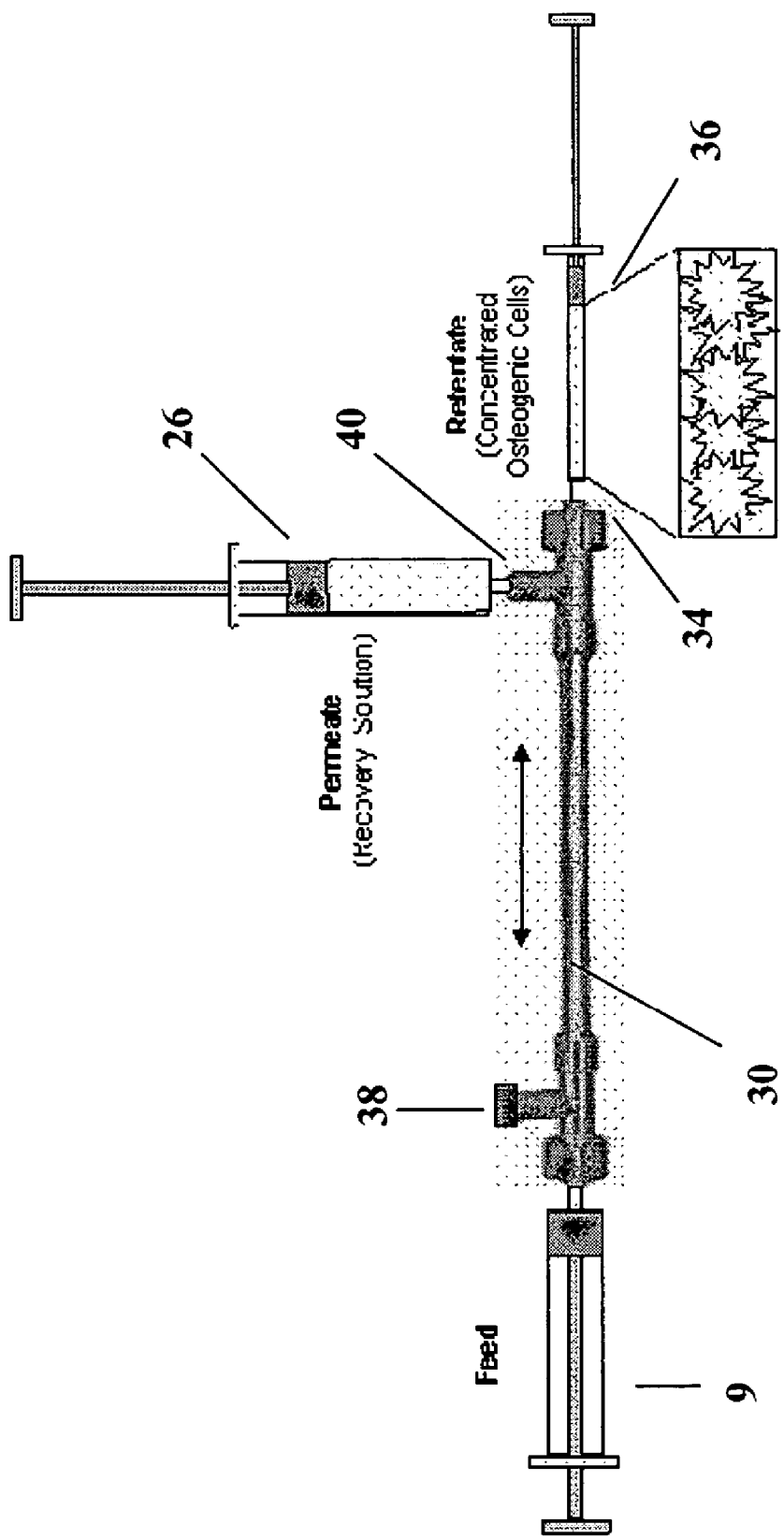
FIG. 6 provides an exemplary schematic showing a concentrate osteogenic cell suspension resulting from operation of second filter. Cross-flow filtration fractionates a portion of the recovery solution from the suspended cells, thereby increasing the concentration of the cells in the retentate syringe.

FIG. 5 shows a schematic drawing of an operation of a second filter, such as a hollow fiber filter, to concentrate the osteogenic cells (i.e., platelets and nucleated cells) recovered from the first filter 12 in FIG. 4, for example. A syringe comprising the osteogenic cells, such as the exemplary syringe 9 from FIG. 4, is connected to the hollow-fiber filter 30, which is operated in cross-flow mode. In cross-flow filtration, the feed stream is recirculated between a feed syringe 9, for example, and retentate syringe 36 tangentially to the membrane in the hollow-fiber filter 30, establishing a pressure differential across the membrane. This causes some of the particles to pass through the membrane. Remaining particles continue to flow across the membrane. Using an appropriate membrane pore size (such as about 0.2 to 0.5 μm), recovery solution, but not cells, are able to pass through the filter membrane of the hollow fiber filter 30. FIG. 6 demonstrates a schematic for showing concentrate osteogenic cell suspension resulting from operation of a second filter. Cross-flow filtration fractionates a portion of the recovery solution from the suspended cells, thereby increasing the concentration of the cells in the retentate syringe 36.

Figure 7:
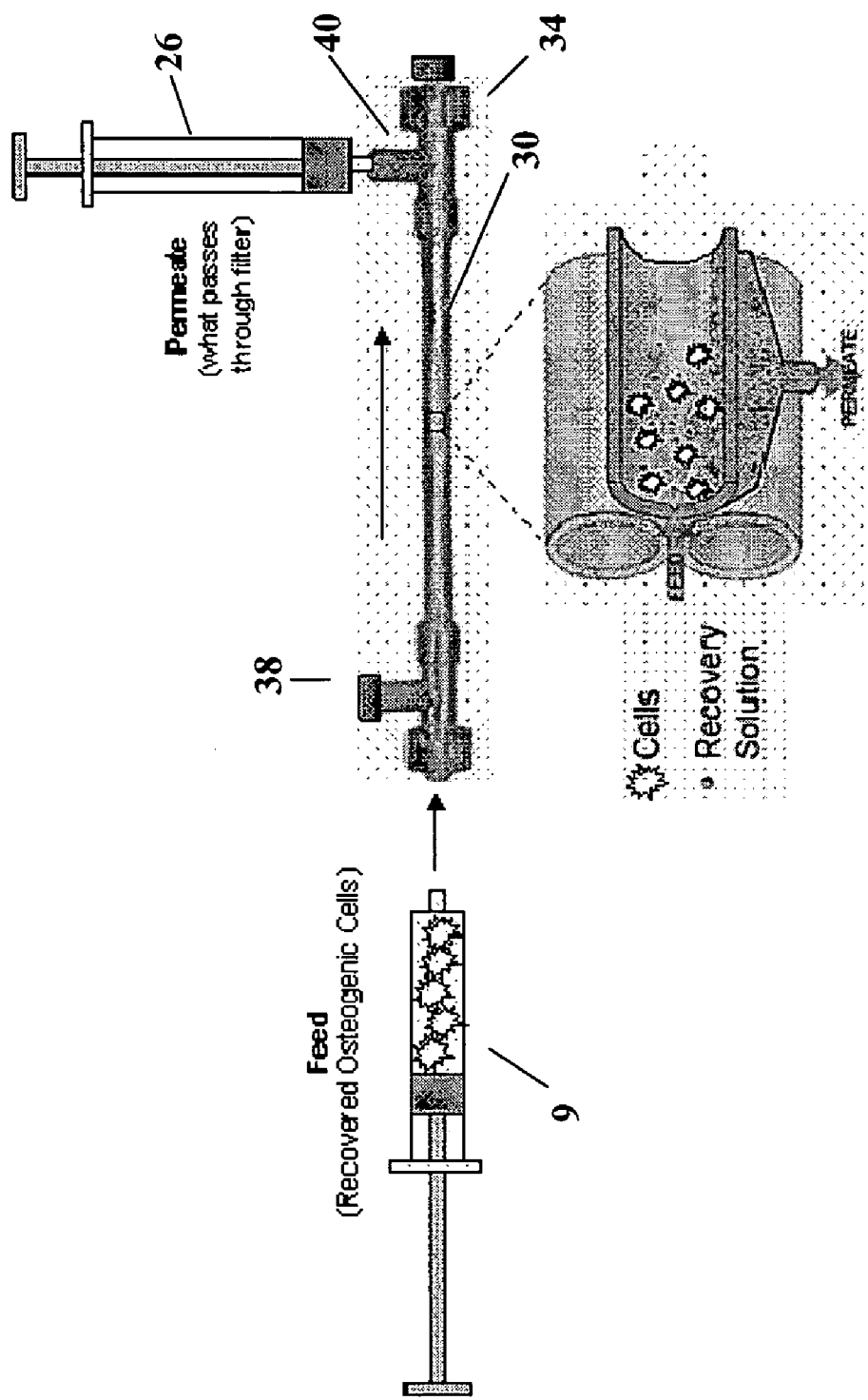
FIG. 7 is an exemplary schematic showing operation of second filter (hollow fiber filter) to concentrate osteogenic cells (i.e., platelets and nucleated cells) recovered from first filter. The syringe containing the recovered osteogenic cells is connected to the hollow-fiber filter, which is operated in dead-end mode (this is accomplished by capping retentate syringe port). Unlike cross-flow filtration, dead end filtration does not involve the recirculation of the feed stream is recirculated between a feed syringe and retentate syringe tangentially to the membrane. Pressure from the advancing feed syringe establishes a pressure differential across the membrane. This causes some of the particles to pass through the membrane. Using an appropriate membrane pore size (0.2 to 0.5 µm), recovery solution, but not cells, are able to pass through the filter membrane of the hollow fiber filter.
Figure 8:
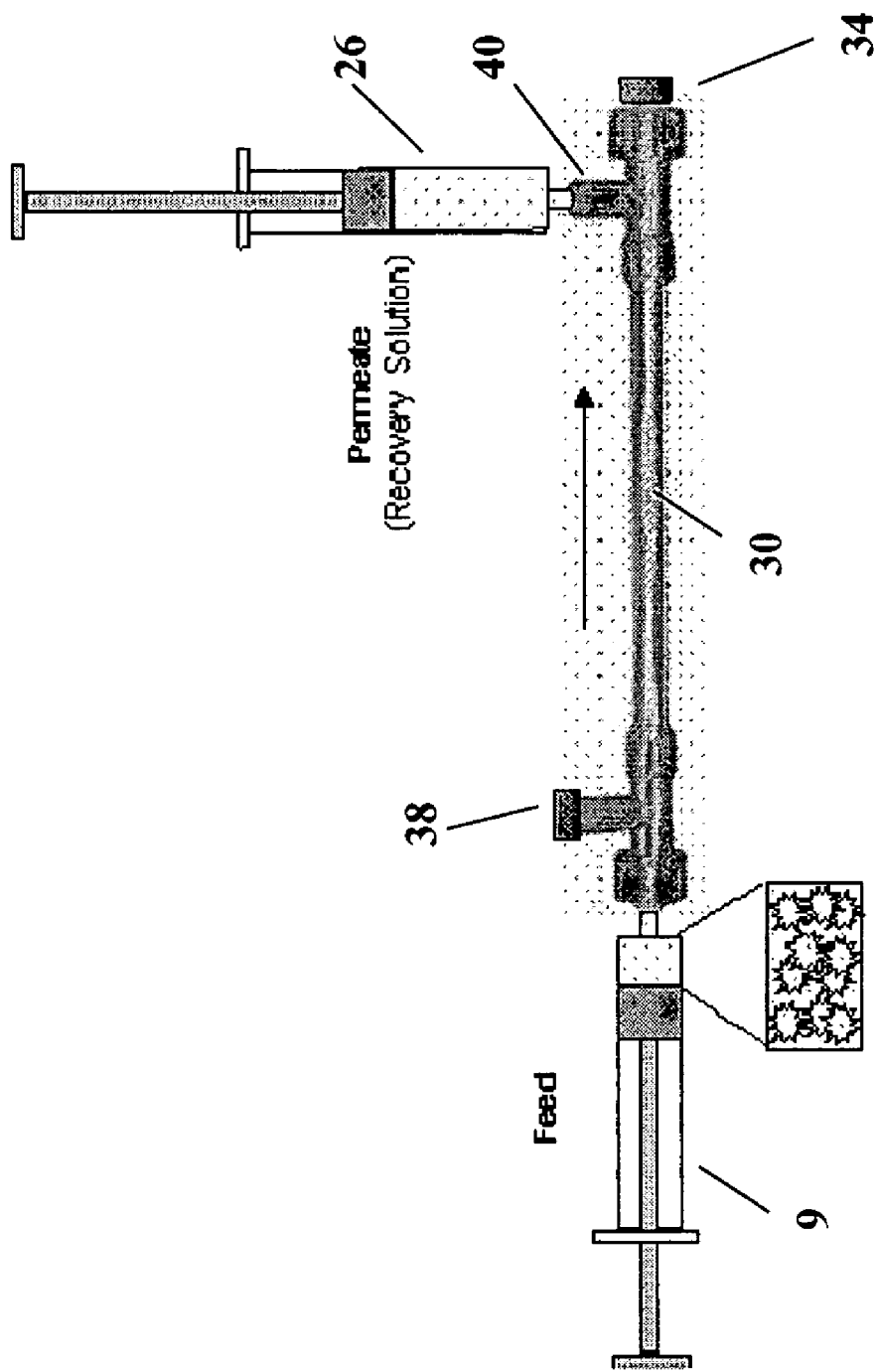
FIG. 8 is an exemplary schematic showing a concentrate osteogenic cell suspension resulting from operation of second filter in dead end mode. Dead end filtration fractionates a portion of the recovery solution from the suspended cells, thereby increasing the concentration of the cells remaining in the feed syringe.

FIG. 7 provides a schematic showing operation of a second filter, such as a hollow fiber filter 30, to concentrate osteogenic cells (i.e., platelets and nucleated cells) recovered from a first filter. The exemplary syringe, such as syringe 9 from FIG. 4, containing the osteogenic cells is connected to the hollow fiber filter 30, which is operated in dead-end mode (this is accomplished by capping the retentate syringe port 34). Unlike cross-flow filtration, dead end filtration does not involve the recirculation of the feed stream between an exemplary feed syringe 9 and retentate syringe tangentially to the membrane. Pressure from the advancing feed syringe establishes a pressure differential across the membrane. This causes some of the particles to pass through the membrane. Using an appropriate membrane pore size (such as about 0.2 to 0.5 μm), recovery solution, but not cells, are able to pass through the filter membrane to the hollow fiber filter 30. FIG. 8 is an exemplary schematic showing a concentrate osteogenic cell suspension resulting from operation of a second filter in dead end mode. Dead end filtration fractionates a portion of the recovery solution from the suspended cells, thereby increasing the concentration of the cells remaining in the feed syringe 9.

Example 3

Description of Cell Concentrate Characteristics

In a particular embodiment of the present invention, the final cell concentrate must have at least one of the following characteristics: 1) nucleated cells per unit volume greater than in the starting physiological solution; 2) platelets per unit volume greater than in the starting physiological solution; and/or 3) upon activation of platelets, the concentration of growth factors is greater than that of an equivalent volume of the starting physiological solution. Examples of growth factors are platelet-derived growth factor (PDGF), transforming growth factor beta (TGF-β), vascular endothelial growth factor (VEGF), epithelial growth factor (EGF), and insulin-like growth factor (IGF).

In particular embodiments, the method to obtain the cell concentrate and/or the cell concentrate itself may have the following attributes: 1) leukocyte concentration of at least about six times that of baseline blood value; 2) substantially no exogenous animal-derived or human-derived constituents in backflush solution (although in alternative embodiments an exogenous animal-derived or human-derived constituent is added, such as the exemplary human serum albumin); 3) substantially no exogenous animal-derived or human-derived constituents in clotting initiator; and/or 4) filter should activate less than about 25% of platelets (Babbush et al., 2003).

In other embodiments, the method to obtain the cell concentrate and/or the cell concentrate itself more preferably has the following attributes: 1) a sole (or first) filter processes a minimum of about 60 mL and maximum of about 120 mL of blood; 2) blood is mixed with at least one anticoagulant; 3) recovery solution comprises biocompatible and/or non-pyrogenic constituents; 4) filtration step(s) takes about 10 minutes or less; 5) filter recovers at least about 70% of platelets from blood; 6) filter concentrates platelets at least about 6-fold compared to baseline physiological solution (such as blood or bone marrow concentrate) value; 7) platelet concentrate comprises sufficient clotting factors for clot initiation (exemplary clotting factors include fibrinogen, Factor V, Factor VII, Factor VIII, Factor IX, Factor X, Factor XI, Factor XII, Factor XIII, prekallikrein, prothrombin, tissue factor, von Willebrand Factor (vWF) (proteins may be monitored during the methods, such as fibrinogen concentration being measured by ELISA)); 8) platelet concentrate clots within about 5 minutes after addition of clot initiator; 9) final clot volume comprises about 5 to 10 mL; and/or 10) once clotted, the concentration of growth factors (such as, for example, PDGF, TGF-β, VEGF, EGF, and IGF) comprises at least about 6 times that of an equivalent or substantially equivalent volume of clotted blood.

In specific embodiments of the present invention, materials utilized in the present invention meet governmental regulatory standards in the art, such as being FDA-approved.

Example 4

Methods to Measure Cell Concentrate Characteristics

Nucleated Cell (Leukocytes) and Platelet Counts (from Wintrobe's Clinical Hematology, 10th ed.)

By exemplary means, leukocytes and platelets can be enumerated by either manual methods and/or automated hematology analyzers, both of which are well known in the art. Manual counts are carried out after appropriate dilution of the sample in a hemocytometer, a specially constructed counting chamber that contains a specific volume. Cells may then be counted, for example, with a microscope.

Automated hematology analyzers increase the accuracy and speed of analysis, and, thus, may be preferable to manual counting. Two exemplary major types of automated counters may be used to enumerate leukocytes and platelets: aperture-impedance counters and optical method counters. Aperture-impedance counters include the Coulter (Hialeah, Fla.), the Sysmex (Baxter Diagnostics, Waukengan, Ill.), and some Cell-Dyne instruments (Abbott Diagnostics, Santa Clara, Calif.), for example. Optical method counters include Technicon (Bayer Diagnostics, Kent, Wash.) and some Cell-Dyn instruments, for example.

Cell counts are determined for the original physiological solution and the final post-processed cell concentrate.

Growth Factor Quantification

Enzyme-linked immunosorbent assays (ELISA) are used to quantify growth factor concentrationk, in exemplary embodiments. Growth factor concentrations are determined for the original physiological solution and the final post-processed cell concentrate after platelet activation. An appropriate platelet activator, such as thrombin, a calcium chloride solution, adenosine diphosphate (ADP), or a combination thereof, may be used to activate platelets. After sufficient time to allow platelet activation and growth factor release (such as less than about one hour), growth factor concentration is quantified, such as by using commercially available ELISA kits.

Example 5

Methods to Remove Fat from the Physiological Solution

In some embodiments of the present invention an additional step or means, such as a filter, is incorporated into the design in order to remove fat from a physiological solution, such as particles (which may include adipocytes). The fat may be cellular or non-cellular in form. Thus, a skilled artisan recognizes that this refers to adipocytes, congealed fat that is non-cellular in nature, or both. A physiological solution is passed through this step or means, such as an exemplary filter referred to herein as a fat reduction filter, in order to substantially reduce (or in some embodiments eliminate) a quantity of fat. The removal of fat will result in faster flow and better osteogenic cell capture as the physiological fluid passes through a subsequent filter(s) in the process. In preferred embodiments, enough fat is removed so that there is no occlusion, blocking, clogging and such of the filter(s). A skilled artisan recognizes that complete removal of fat or adipocytes is desirable, but unnecessary so long as filtration is achievable.

Commercially available filters that have been used clinically to remove microaggregates from blood may be suitable for this application. Examples include but are not limited to standard blood transfusion filters, such as the SQ40SJKL (Pall Corp., Port Washington, N.Y.) and LipiGuard (Pall Corp., Port Washington, N.Y.).

FIGS. 9A-9E show a schematic of the incorporation of a fat reduction filter 8 into the device used to prepare an osteogenic cell concentrate. The physiological solution is passed via syringe 6 through the exemplary fat reduction filter 8 component into a collection bag 10 (FIG. 9A). The fluid, reduced in fat particle content, is then processed through the leukofilter 12 as shown in FIGS. 4 and 9. If necessary, the cell suspension recovered from the leukofilter 12 is then processed through the hollow fiber filter 30 in either cross-flow mode (FIGS. 5 and 6) or dead-end mode (FIGS. 7 and 8).

Example 6

Bone Marrow Aspirate (BMA) Filtration in Immature New Zealand White Rabbits BMA was taken from two skeletally immature New Zealand White rabbits and processed through an exemplary filter of the present invention to demonstrate an increase in the concentration of nucleated cells (a cell population that, in some embodiments, includes undifferentiated cells, such as osteoprogenitors). This study showed that the filters were able to concentrate BMA from immature New Zealand White rabbits within a targeted range (about 6 to 10-fold) in a specified timeframe (under about 15 minutes).

Materials and Methods

Blood and bone marrow aspirate (BMA) were drawn from three skeletally immature New Zealand White rabbits. Each rabbit was 2 months old and weighed approximately 1.4 kg at the time of the procedure. The rabbits were not treated with any medications or steroids prior to BMA harvest. Anesthesia was induced by intramuscular administration of 50 mg/kg of ketamine and 10 mg/kg of Xylazine. Approximately 2-mL of blood was drawn from the aorta of each rabbit and mixed with 0.3-mL of heparinized saline. The volume of blood drawn from each rabbit is listed in Table I. Bone marrow was bilaterally aspirated from the proximal tibias of each rabbit. A 0.5 to 1-cm incision was made on the medial aspect of anterior proximal metaphysis of the tibia. An 18-g needle was rotated gently to perforate the cortical bone and enter the marrow cavity. If the initial needle clogged during the perforation, the needle was replaced with a new one. Negative pressure was established by drawing the plunger back until marrow began flowing into the syringe; the pressure was then reduced, and the marrow was collected for about 10 seconds. For each tibia, two to 3.5-mL of BMA was aspirated using an 18-g needle into a 10 cc disposable syringe filled with 0.5-mL of heparinized saline (1000 units/mL). The syringe was detached and was inverted several times to ensure complete mixing, and then the BMA was transferred to a sterile, graduated plastic test tube. The volume of BMA drawn from each rabbit is listed in Table II.

The initial count of nucleated cells in each sample was determined by lysing the red blood cells in a 2% acetic acid solution. One hundred μL of aspirate was mixed with 900-μL of acetic acid. A portion of the resultant cell suspension was injected into a hemocytometer grid and cells were counted using a compound microscope (BX60, Olympus Optical Co., Ltd., Japan) at 200× magnification. Nucleated cell concentration was calculated as:

$$N = C \times SF \times D_{acetic\ acid}$$

where N=nucleated cell concentration; SF=scale factor of hemocytometer grid=104; and $D_{acetic\ acid}$=dilution factor in acetic acid=10. At least two replicate counts were performed for each sample.

After determination of initial nucleated cell count, four-ml of BMA from each rabbit were pooled to yield a combined volume of 12-mL. The pooled BMA sample was then passed through the exemplary filtration device as shown schematically in FIGS. 5, 6, and 10. In FIGS. 10A-10E, the aggregate filter 7 may remove large particles of material, which in certain embodiments comprises fat particles.

This particular embodiment comprises a system having at least a one-step process utilizing a leukoreduction filter to capture osteogenic cells and, optionally, a hollow fiber filter to concentrate the captured cells. The leukoreduction filter (P/N B-1462G; L/N 312700) and recovery solution (L/N SLS051303) were manufactured by Pall Medical, Inc. (Port Washington, N.Y.). The hollow fiber filter (P/N X12E-100-20N; L/N DH157/N) was made by Spectrum Laboratories, Inc. (Rancho Dominguez, Calif.). The nucleated cell concentration of the ACS-processed cell suspension was determined as described in the preceding paragraph.

Results

Figure 11:
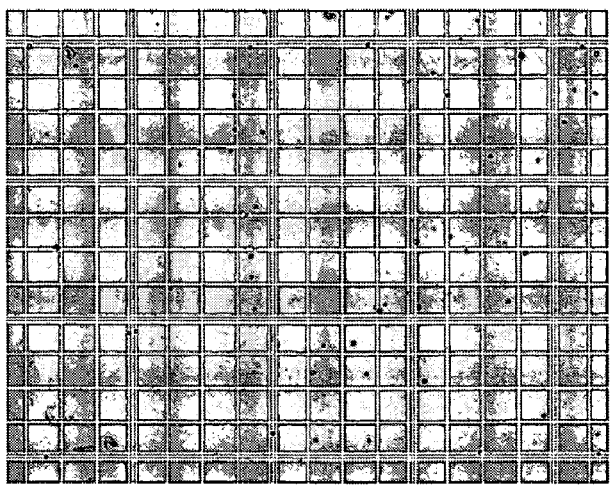
FIG. 11 shows representative fields of view of nucleated cell counts of blood, pre-processed BMA, and post-processed BMA.
Figure 11:
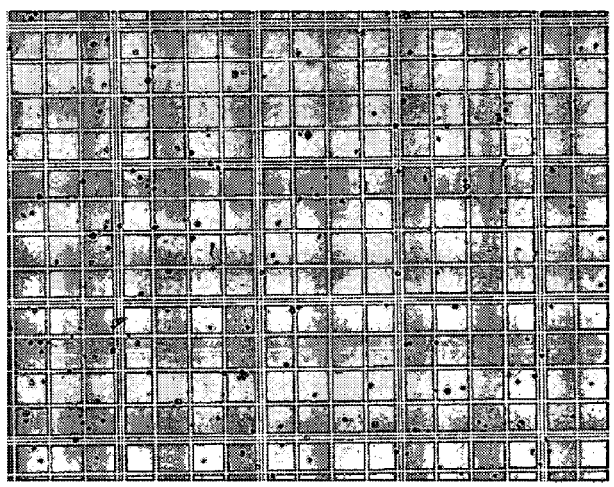
Figure 11:
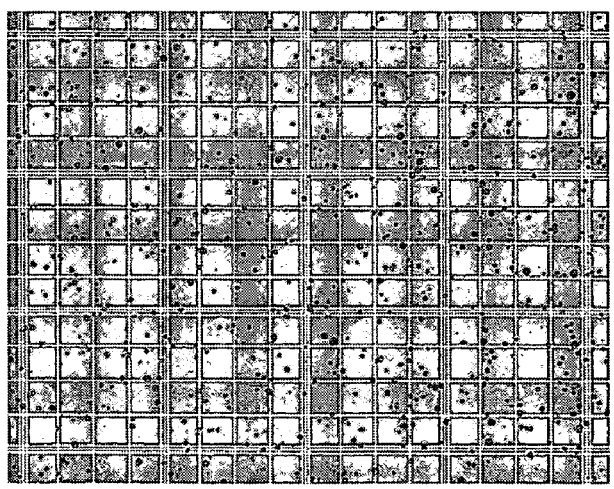

The mean nucleated cell counts of the blood, pre-processed BMA, and post-processed BMA were $6.0 \times 10^6$, $20.1 \times 10^6$, and $131 \times 10^6$ cells/ml (Tables I, II, and III, respectively). Representative fields of view of cells in the hemocytometer are shown in FIG. 11. The nucleated cell count of the pre-processed BMA was approximately 3.5 times that of blood (Holdrinet et al., 1980). This indicates that bone marrow cells were collected in the aspirate; BMA composed entirely of peripheral blood would have a nucleated cell count similar to that of blood. Twelve mL of BMA pooled from the three donor rabbits was processed through the ACS prototype in approximately 5 minutes. The final volume was 0.6-mL, representing a 20-fold decrease in volume. The cell concentration of the post-filtered sample was approximately 6.5 times that of the pre-processed BMA. Given that a 20-fold decrease in volume resulted in a 6.5-fold increase in cell concentration, the cell recovery efficiency of the filtration prototype was 33%.

This study showed that the prototype filters were able to concentrate BMA from skeletally immature New Zealand White rabbits within the targeted range (about 6- to 10-fold) and timeframe (under about 15 minutes). Given that age-related changes in marrow cellularity and fat composition in rabbits are known (Kita et al., 1987; Bigelow and Tavassoli, 1984), in alternative embodiments the present invention provides filtration of concentrate nucleated cells in BMA from skeletally mature rabbits.

TABLE I

Volume and nucleated cell counts for blood samples from individual rabbits

| Sample | Blood Volume (ml) | Replicate Cell Counts | Nucleated Cell Concentration ($10^6$/ml) |
|---|---|---|---|
| Rabbit 1 | 2.8 | 88; 119; 91 | 9.7 |
| Rabbit 2 | 1.4 | 32; 48; 40 | 4.0 |
| Rabbit 3 | 1.8 | 43; 49; 36 | 4.2 |
| | | | Mean = 6.0 ± 3.2 |

TABLE II

Volume and nucleated cell counts for unprocessed bone marrow aspirate (BMA) samples from individual rabbits

| Sample | BMA Volume (ml) | Replicate Cell Counts | Nucleated Cell Concentration ($10^6$/ml) |
|---|---|---|---|
| Rabbit 1 | 8 | 214; 229 | 22.2 |
| Rabbit 2 | 7 | 203; 180 | 19.2 |
| Rabbit 3 | 5 | 172; 213; 183 | 18.9 |
| | | | Mean = 20.1 ± 1.8 |

TABLE III

Volume and nucleated cell counts for filtration-processed bone marrow aspirate. Four ml of marrow was taken from each of the three rabbits and processed through the filtration system.

| Sample | Starting Volume (ml) | Final Volume (ml) | Replicate Cell Counts | Nucleated Cell Concentration ($10^6$/ml) |
|---|---|---|---|---|
| Filtration-Processed BMA | 12 | 0.6 | 989; 1590; 1335 | 131 ± 30 |

Example 7

Method to Activate Platelets and Coagulate Cell Concentrate

A platelet activation agent (e.g., calcium chloride solution or thrombin, or a combination thereof) may be added to the cell concentrate in order to activate platelets and induce coagulation. The addition of the platelet activator to the cell concentrate will result in a higher growth factor concentration (due to increased platelet activation) and better handling characteristics (due to coagulation), in preferred embodiments.

The platelet activator should be added to the cell concentrate at an appropriate ratio to induce rapid platelet activation (less than 30 minutes) and coagulation. For example, a 1:10 activator:cell concentrate ratio is used when the activator is a $CaCl_2$/thrombin (100 units/ml) solution.

A portion of the cell concentrate prepared for each blood donor is added to a glass beaker, and a coagulum is formed by the addition of an appropriate platelet activator. The mixture is allowed to undergo clot retraction for an appropriate time period (at least about 30 minutes). The contents of the beaker will then be transferred to centrifuge tubes and centrifuged at about 1,000 g for about 30 minutes. The growth factor concentration in the supernatant is quantified by commercially available enzyme-linked immunosorbent assays (ELISA) kits, in exemplary embodiments. For reference, this experiment is repeated for: (i) an unprocessed blood sample from each donor; and/or (ii) a portion of the cell concentrate to which no platelet activator is added.

Example 8

Preparation of a Platelet Rich Concentrate (PRC) from Human Blood Using a Single Filter Whole blood was taken from healthy human donors and processed through an exemplary filter of the present invention to demonstrate at least an increase in the concentration of platelets and platelet-derived growth factors. This study showed that processing of human blood through a single filter (for example, a leukoreduction filter) was able to concentrate platelets and growth factors above baseline values observed for unprocessed blood.

Figure 12:
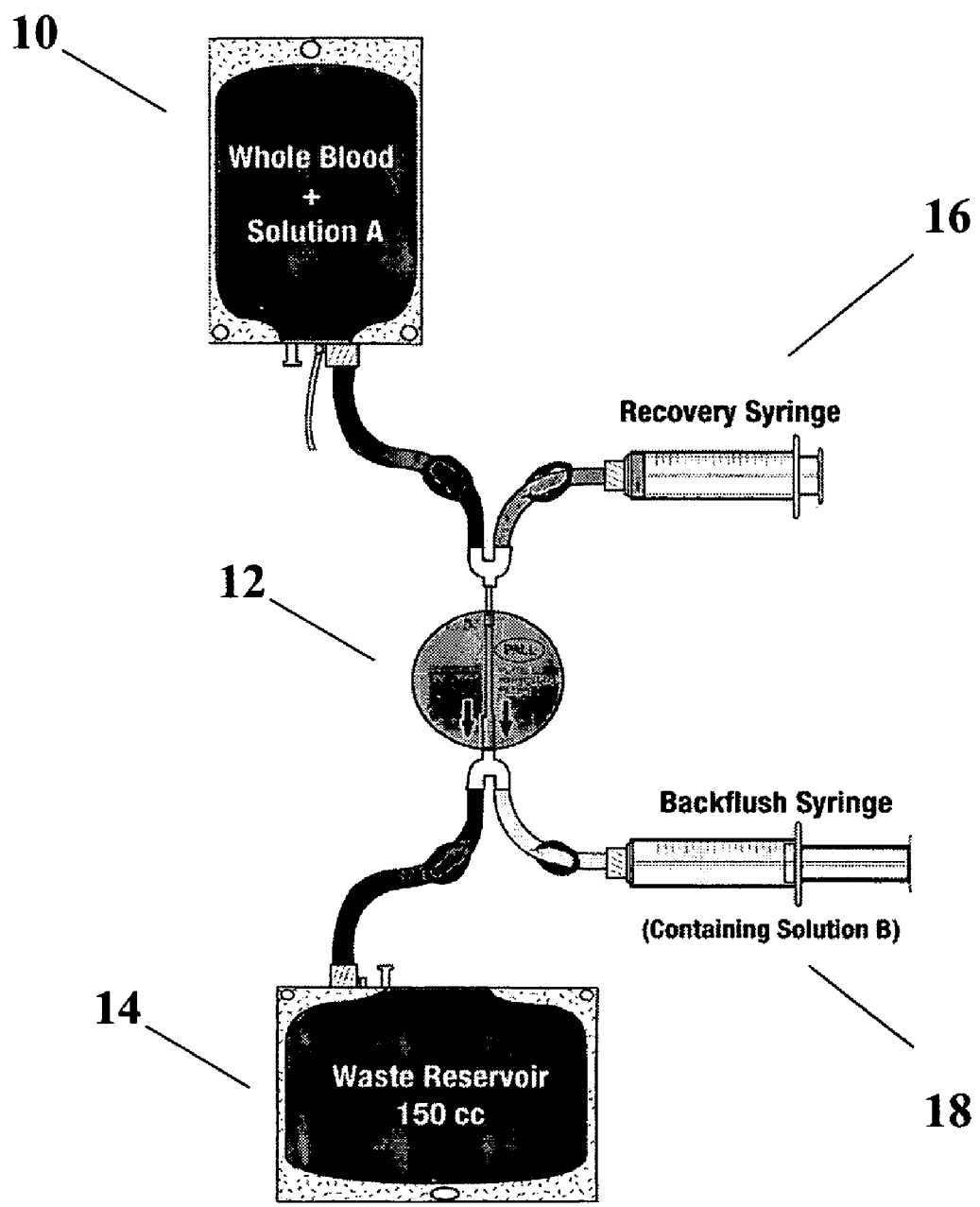
FIG. 12 illustrates a schematic of an exemplary filter configuration used to prepare platelet rich concentrate from blood.

A schematic of the filter that was evaluated is shown in FIG. 12. Each prototype comprised two standard 150-cc blood collection bags, a leukoreduction filter, and two ports for syringe attachment. To evaluate the filters, units of whole blood (each unit was 450-ml) were collected from healthy human volunteers into blood bags containing 50-ml of Anticoagulant Citrate Dextrose, formula A (ACD-A). Sixty ml aliquots were transferred into a 60-ml syringe. The contents of the syringe were then injected into a blood bag comprising 10-ml of platelet capture solution A (water for injection). In some cases, 120-ml of anticoagulated blood was injected into a bag comprising 20-ml of solution A to determine if the filters could effectively process a double dose of blood. The blood bag comprising the diluted blood sample was attached to a platelet recovery filter (Purecell PL, Pall Medical, Inc., Port Washington, N.Y.). The filtration height (vertical distance between top of blood line in collection bag and entry point into drain bag) was adjusted to 12.5 inches. The diluted blood sample was then filtered at room temperature. The filtration time for each sample was recorded. After filtration was complete, the filter was backflushed with a syringe filled with 7-ml of platelet recovery solution B (5% saline solution) and 13-cc of air. The contents of the filter were backflushed into a 20 cc syringe. The recovered cellular suspension was transferred from the syringe into a 15-ml centrifuge tube. The total volume of the recovered platelets was measured using the graduated markings on the centrifuge tube.

For each donor, platelet concentration was measured for the recovered cell suspension and whole blood samples using a Cell Dyn Hematology Analyzer (Abbott Labs, IL). ELISAs for PDGF-AB, TGF-β1, and VEGF-A (Quantikine, R&D Systems, Minneapolis, Minn.) were performed on the recovered suspension, the recovered suspension+10% $CaCl_2$/thrombin (5000 Units/ml), and whole blood. Significant differences in means were determined by ANOVA at a 95% confidence level.

Filtration time ranged from 10 to 15 minutes for the 60-ml blood samples (n=20) and from 45 to 90 minutes for the 120-ml samples (n=9). The flow rate of the 120-ml samples was slowed by backpressure from the drain bag as it filled to near maximum capacity. The final volume of the recovered cell suspension (for both starting blood volumes) ranged from 9 to 10-ml, averaging 9.5-ml.

Figure 13:
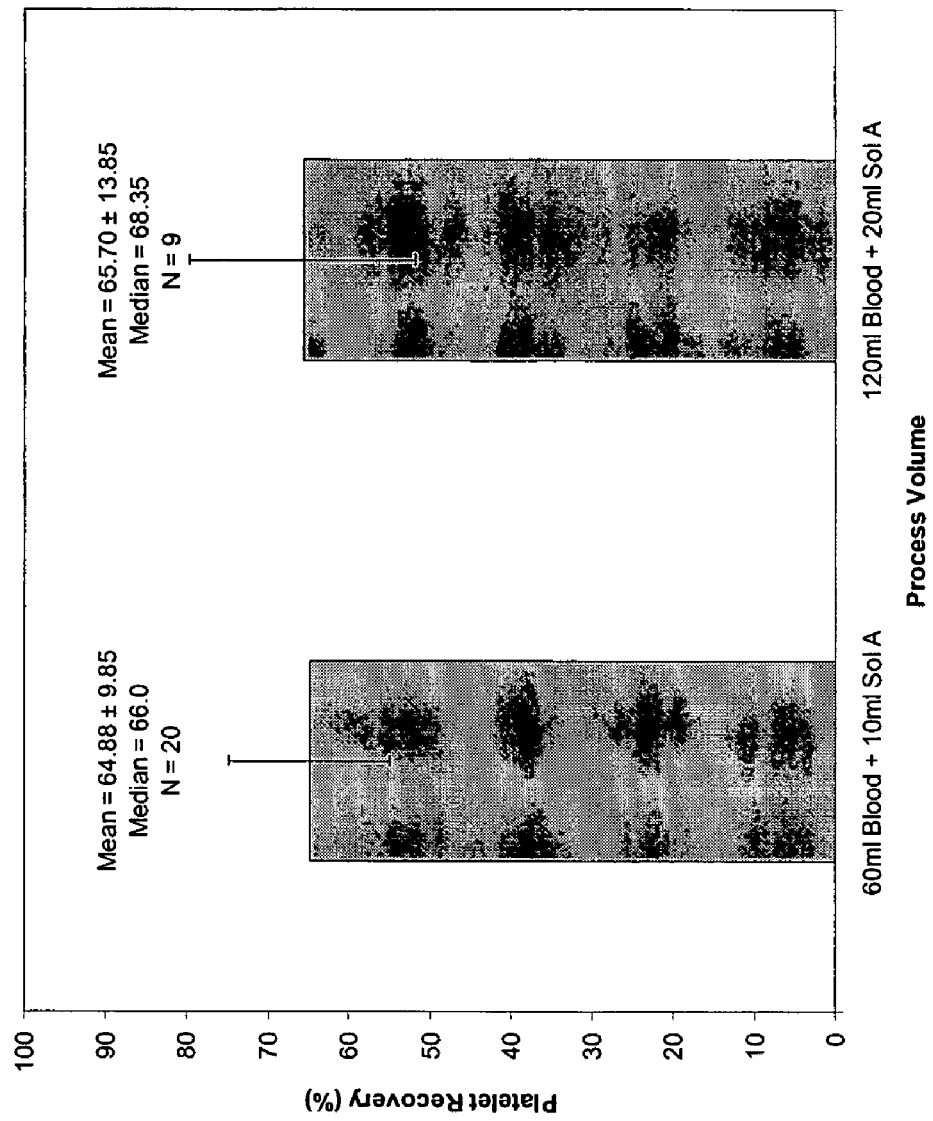
FIG. 13 demonstrates platelet recovery for two exemplary starting blood volumes.

The mean platelet recovery was approximately 65% for both the 60-ml and 120-ml blood samples and did not differ significantly between the two groups (FIG. 13). The mean platelet concentration factors were 4.1±0.4 fold and 8.3±1.2 fold for the 60-ml and 120-ml samples, respectively, compared to whole blood (p<0.05).

Figure 14:
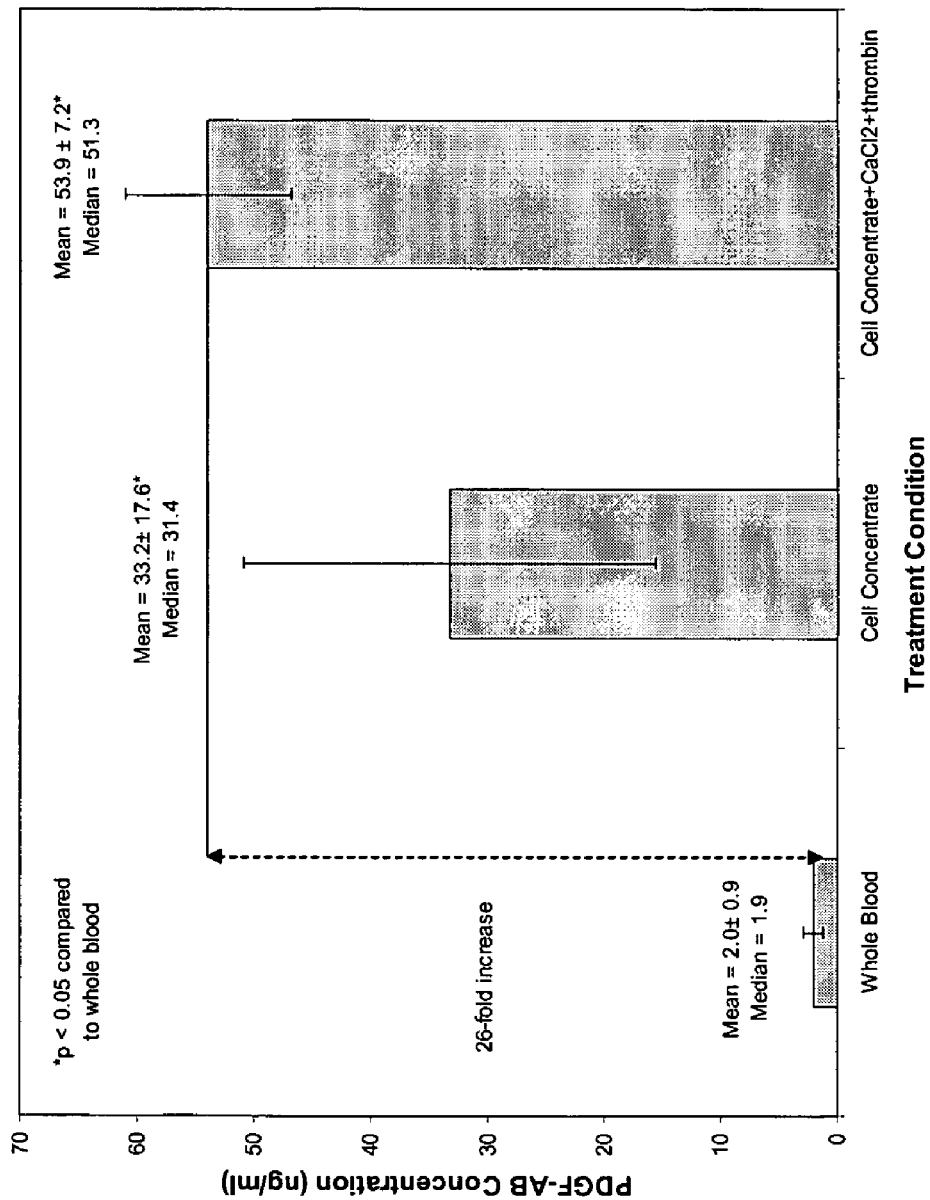
FIG. 14 shows concentration of PDGF-AB in whole blood and recovered platelets.
Figure 15:
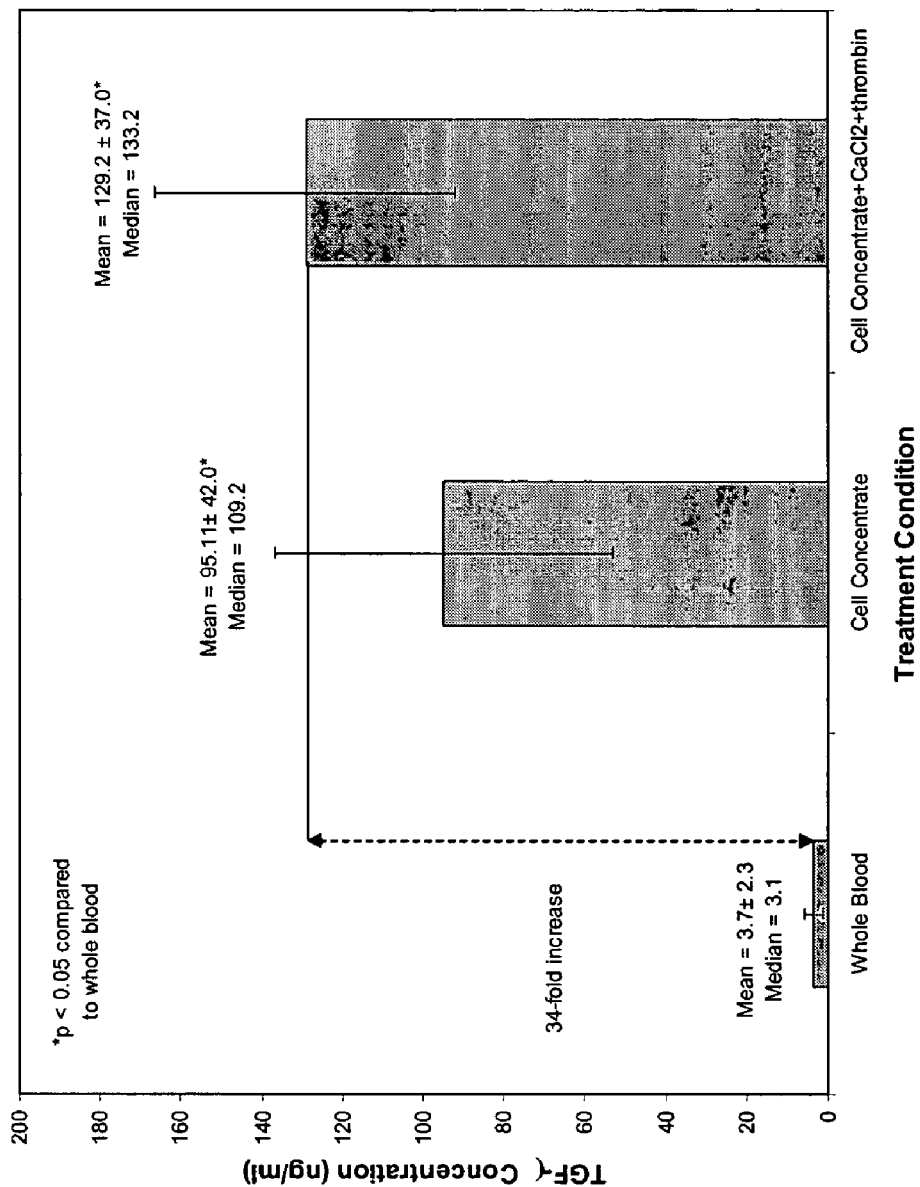
FIG. 15 shows concentration of TGF-β1 in whole blood and recovered platelets.
Figure 16:
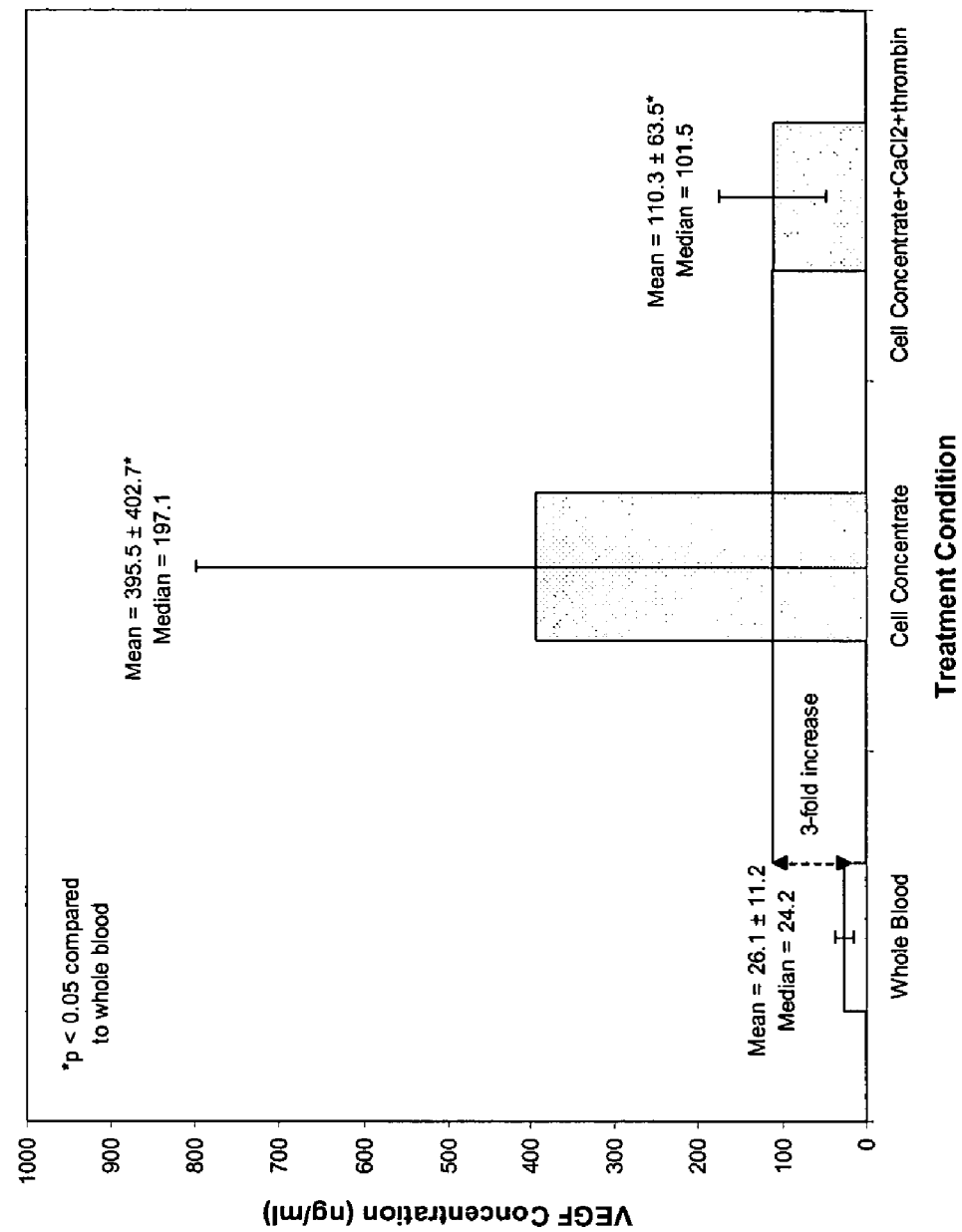
FIG. 16 shows concentration of VEGF in whole blood and recovered platelets.

The mean concentrations of PDGF-AB, TGF-β1, and VEGF-A in whole blood and the platelet concentrate are shown in FIGS. 14-16, respectively (n=15). The cell concentrate produced by the filter showed 16-fold, 25-fold, and 14-fold increases in PDGF, TGF-β, and VEGF concentrations, respectively, compared to whole blood (p<0.05 in all cases). When the cell concentrate was activated with calcium chloride/thrombin, the concentration factor increased to 26-fold and 34-fold for PDGF and TGF-β, respectively (p<0.05 in both cases). The VEGF concentration factor dropped from 14-fold to 3-fold upon activation with calcium chloride/thrombin. In a specific embodiment, this is related to the apparent ability of fibrin to bind VEGF, possibly masking the ELISA epitope.

This study showed that an exemplary filter of the present invention is useful for conveniently preparing a platelet rich concentrate from whole blood. The filtration process took 10 to 15 minutes and produced a final 9.5-ml product with greater than 4-fold enrichment in platelets. Additionally, the concentrations of PDGF-AB, TGF-β1, and VEGF-A were significantly higher in the platelet concentrate compared to whole blood.

REFERENCES

All patents and publications mentioned in the specification are indicative of the level of those skilled in the art to which the invention pertains. All patents and publications are herein incorporated by reference in their entirety to the same extent as if each individual publication was specifically and individually indicated to be incorporated by reference.

Patents

U.S. Pat. No. 5,824,084
U.S. Pat. No. 6,010,627
U.S. Pat. No. 6,049,026
U.S. Pat. No. 6,342,157
U.S. Pat. No. 6,398,972
WO 96/27397 PCT Application Publications Babbush C A, Kevy S V, Jacobson M S. An in vitro and in vivo evaluation of autologous platelet concentrate in oral reconstruction. Implant Dent. 2003; 12(1):24-34.
Bigelow C L and Tavassoli M, "Fatty involution of bone marrow in rabbits", Acta Anat (Basel), 118(1):60-4 (1984).
Connolly, J., Guse, R., Lippiello, L., Dehne, R. Development of an Osteogenic Bone-Marrow Preparation, J. Bone and Joint Surgery, vol. 71-A, no. 5, pp. 684-691, 1989.
Holdrinet R S G, Egmond J V, Wessels J M C, and Haanen C, "A method for quantification of peripheral blood admixture in bone marrow aspirates", Exp. Hemat., 8(1): 103-7 (1980).
Kita K, Kawai K, and Hirohata K, "Changes in bone marrow blood flow with aging", J Orthop Res, 5(4):569-75 (1987).
Takigami, H., Muschler, G. F., et al. Spine Fusion using Allograft bone matrix enriched in bone marrow cells and connective tissue progenitors, Trans. of 48$^{th}$ Orthopaedic Res. Soc., p. 807, 2002.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

We claim:

1. A method of preparing a cell concentrate comprising the steps of:
   providing a physiological fluid which has not been previously subjected to centrifugation and which comprises platelets, plasma, nucleated cells and red blood cells,
   combining a hypotonic fluid with the physiological fluid, the hypotonic fluid being in an amount which does not cause the cells to lyse in the physiological fluid/hypotonic fluid combination,
   subjecting the combined physiological fluid/hypotonic fluid to a filter to produce a filter retentate and a permeate fluid, wherein said filter retentate comprises platelets and nucleated cells per unit volume greater than in the physiological fluid and wherein said permeate fluid comprises plasma and red blood cells, and
   removing the filter retentate from the filter to produce the cell concentrate.

2. The method of claim 1, wherein the physiological fluid comprises bone marrow aspirate, blood, or a mixture thereof.

3. The method of claim 1, wherein said nucleated cells comprise leukocytes, stem cells, connective tissue progenitor cells, osteoprogenitor cells, chondroprogenitor cells, or a mixture thereof.

4. The method of claim 1, wherein the stem cells are mesenchymal stem cells, hematopoietic stem cells, or both.

5. The method of claim 1, wherein the hypotonic fluid is water.

6. The method of claim 1, wherein the hypotonic fluid comprises sodium chloride.

7. The method of claim 1, further comprising delivering the filter retentate removed from the filter to a bone defect in an individual.

8. The method of claim 1, wherein said method farther comprises the step of admixing a scaffold material to the filter retentate removed from the filter to produce a scaffold material/filter retentate mixture.

9. The method of claim 8, further comprising the step of delivering the scaffold material/filter retentate mixture to a bone defect in an individual.

10. The method of claim 8, wherein the scaffold material is comprised of a block, paste, dust, cement, powder, granule, putty, liquid, gel, solid, or a mixture thereof.

11. The method of claim 8, wherein the scaffold material is comprised of a ceramic, a polymer, a metal, allografi bone, autografi bone, demineralized bone matrix, or a mixture thereof.

12. The method of claim 8, wherein the scaffold material is biodegradable.

13. The method of claim 8, wherein the scaffold material is osteoconductive, osteogenic, osteoinductive, or a combination thereof.

14. The method of claim 8, wherein the scaffold material is comprised of synthetic material, natural material, or a combination thereof.

15. The method of claim 8, said method further comprising the step of admixing a biological agent with the filter retentate removed from the filter, the scaffold material, or a combination thereof.

16. The method of claim 15, wherein the biological agent admixed with the scaffold material is further defined as the biological agent being comprised on the scaffold material, in the scaffold material, or both.

17. The method of claim 8, further comprising the step of admixing a clotting initiator with the scaffold material/filter retentate mixture, the scaffold material, or both.

18. The method of claim 1, wherein the filter retentate removed from the filter is subjected to at least one further processing step.

19. A method of preparing a cell concentrate comprising the steps of:
    providing a physiological fluid which has not been previously subjected to centrifugation and which comprises platelets, plasma, nucleated cells and red blood cells,
    combining a hypotonic fluid with the physiological fluid, the hypotonic fluid being in an amount which does not cause the cells to lyse in the physiological fluid/hypotonic fluid combination,
    subjecting the combined physiological fluid/hypotonic fluid to a leukocyte reduction filter to produce a filter retentate and a permeate fluid, wherein said filter retentate comprises platelets and nucleated cells per unit volume greater than in the physiological fluid and wherein said permeate fluid comprises plasma and red blood cells, and
    removing the filter retentate from the filter to produce the cell concentrate.

* * * * *